(12) United States Patent
Eddy et al.

(10) Patent No.: US 10,814,048 B2
(45) Date of Patent: Oct. 27, 2020

(54) PORTABLE PUMP FOR NEGATIVE PRESSURE WOUND THERAPY

(71) Applicant: Parasol Medical LLC, Buffalo Grove, IL (US)

(72) Inventors: Patrick E. Eddy, Allendale, MI (US); Lucas W. Stephens, Lowell, MI (US); Jacob D. Stephens, Lowell, MI (US); Camryn R. Delooff, Munster, IN (US); Michael D. Kilcran, Buffalo Grove, IL (US)

(73) Assignee: Parasol Medical LLC, Buffalo Grove, IL (US)

( * ) Notice: Subject to any disclaimer, the term of this patent is extended or adjusted under 35 U.S.C. 154(b) by 513 days.

(21) Appl. No.: 15/586,385

(22) Filed: May 4, 2017

(65) Prior Publication Data

US 2017/0319758 A1    Nov. 9, 2017

Related U.S. Application Data

(60) Provisional application No. 62/331,668, filed on May 4, 2016.

(51) Int. Cl.
*A61M 1/00*    (2006.01)

(52) U.S. Cl.
CPC .......... *A61M 1/007* (2014.02); *A61M 1/0003* (2013.01); *A61M 1/0009* (2013.01); *A61M 1/0068* (2014.02); *A61M 1/0027* (2014.02); *A61M 1/0031* (2013.01); *A61M 1/0088* (2013.01); *A61M 1/0094* (2014.02); *A61M 2205/073* (2013.01); *A61M 2205/18* (2013.01);

(Continued)

(58) Field of Classification Search
CPC .............. A61M 1/0088; A61M 1/0027; A61M 1/0068; A61M 1/0003; A61M 1/0009; A61M 1/0023; A61M 1/0031; A61M 2205/073; A61M 27/00; A61M 2205/071; A61M 2205/18; A61M 2205/3331; A61M 2205/581; A61M 2205/587
See application file for complete search history.

(56) References Cited

U.S. PATENT DOCUMENTS 4,392,858 A    7/1983   George et al.
5,279,550 A    1/1994   Habib et al.
(Continued)

FOREIGN PATENT DOCUMENTS

WO    2009137194 A2    11/2009

*Primary Examiner* — Dominick L Plakkoottam
(74) *Attorney, Agent, or Firm* — Price Heneveld LLP

(57) ABSTRACT

A portable pump is provided for negative pressure wound therapy for drawing a vacuum from a wound site via a tube. The pump includes an inlet configured to attach the tube from the wound site; a canister in fluid communication with the inlet for collecting fluids drained from the wound site; and a manually-actuated pump mechanism for creating the vacuum. The pump mechanism includes a vacuum chamber in fluid communication with the canister; a piston disposed in the vacuum chamber; and a pump handle coupled to the piston to move the piston in the vacuum chamber between first and second positions to create the vacuum. The pump handle moving between a retracted position and an extended position. The piston is in the first position when said pump handle is in the retracted position and is in the second position when said pump handle is in the extended position.

39 Claims, 20 Drawing Sheets

(52) U.S. Cl.
CPC ............ *A61M 2205/3331* (2013.01); *A61M 2205/3337* (2013.01); *A61M 2205/3379* (2013.01); *A61M 2205/3382* (2013.01); *A61M 2205/502* (2013.01); *A61M 2205/581* (2013.01); *A61M 2205/587* (2013.01); *A61M 2205/8206* (2013.01)

(56) References Cited

U.S. PATENT DOCUMENTS

| | | | |
|---|---|---|---|
| 5,830,198 A | 11/1998 | Henniges et al. | |
| 6,174,306 B1* | 1/2001 | Fleischmann | A61B 17/085 604/540 |
| 6,261,276 B1* | 7/2001 | Reitsma | A61M 1/0023 604/319 |
| 10,328,188 B2* | 6/2019 | Deutsch | F16M 13/022 |
| 2010/0036333 A1 | 2/2010 | Schenk, III et al. | |
| 2010/0042074 A1 | 2/2010 | Weston et al. | |
| 2012/0078170 A1 | 3/2012 | Smith et al. | |
| 2012/0209225 A1* | 8/2012 | Hu | A61M 1/0096 604/319 |
| 2013/0144227 A1* | 6/2013 | Locke | A61M 1/0031 604/318 |
| 2014/0115893 A1* | 5/2014 | Pratt | A61M 1/0031 29/890.09 |
| 2015/0018784 A1* | 1/2015 | Coulthard | A61M 1/0068 604/319 |
| 2016/0045648 A1 | 2/2016 | Locke et al. | |

* cited by examiner

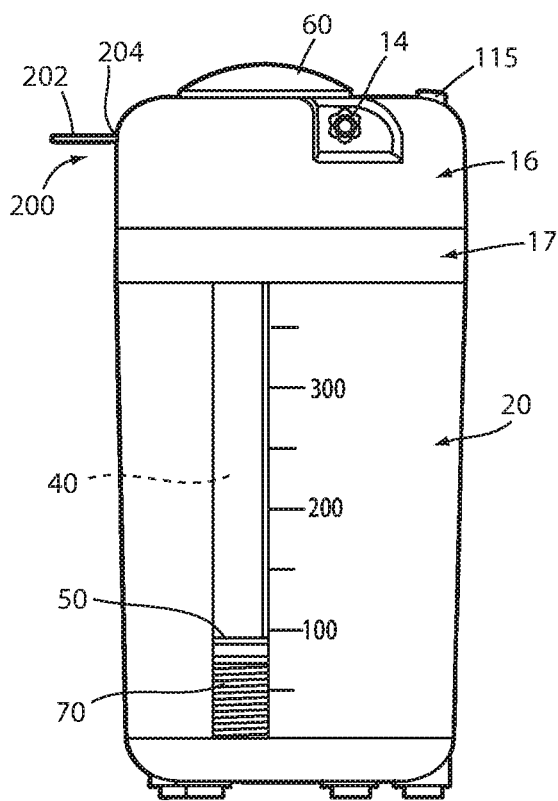
FIG. 26
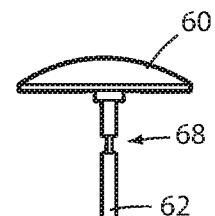
FIG. 27
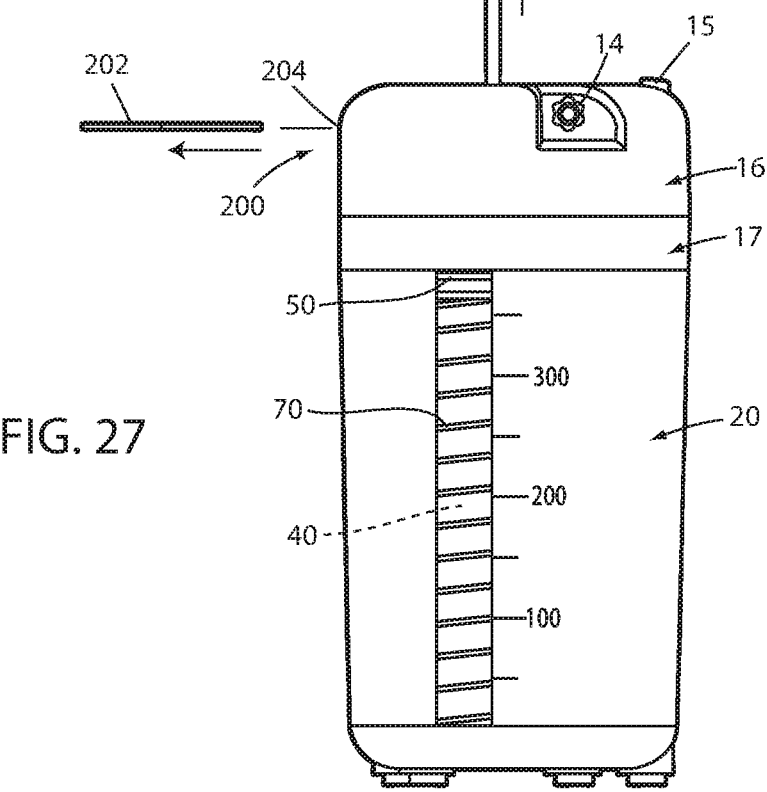

PORTABLE PUMP FOR NEGATIVE PRESSURE WOUND THERAPY

CROSS-REFERENCE TO RELATED APPLICATION

This application claims priority to and the benefit under 35 U.S.C. § 119(e) of U.S. Provisional Patent Application No. 62/331,668, filed on May 4, 2016, entitled "PORTABLE PUMP FOR NEGATIVE PRESSURE WOUND THERAPY," by Patrick E. Eddy, the entire disclosure of which is incorporated herein by reference.

FIELD OF THE INVENTION

The present invention generally relates to a portable pump, and more particularly, a portable pump for negative pressure wound therapy.

BACKGROUND OF THE INVENTION

Wound treatment systems that treat a wound using a vacuum are known. Examples of such systems are disclosed in U.S. Pat. Nos. 4,382,441; 4,392,858; 4,655,754; 4,826,494; 4,969,880; 5,100,396; 5,261,893; 5,527,293; 5,636,643; 5,645,081; 6,071,267; 6,117,111; 6,135,116; 6,142,982; 6,174,306; 6,345,623; 6,398,767; 6,520,982; 6,553,998; 6,814,079; 7,198,046; 7,216,651; 8,007,491; 8,128,607; 8,162,908; 8,177,764; 8,337,474; and 8,529,532. These systems utilize either a manual pump or an automated vacuum pump to draw air and fluid secretions from the wound site. The systems that use an automated pump are expensive, and the patient is typically required to pay a rental fee and return the pump when finished. Moreover, the automatic pumps are heavy and are generally not portable, let alone wearable.

The systems that utilize the manual pumps are generally very simple in design in that they may include a syringe that the nurse or patient pulls back on the piston handle to draw fluid from the wound or a bulb that is pumped. For those with a syringe, once the fluid fills the syringe, the syringe is removed and disposed of. However, such manual pumps do not allow the user to select a pressure level and do not prompt the user to increase the pressure by manually pumping when the pressure drops.

SUMMARY OF THE INVENTION

According to one aspect of the present invention, a portable pump is provided for negative pressure wound therapy for drawing a vacuum from a wound site via a tube, the portable pump comprising: an inlet configured to attach the tube from the wound site; a canister in fluid communication with the inlet for collecting fluids drained from the wound site; and a manually-actuated pump mechanism for creating the vacuum. The manually-actuated pump mechanism comprises: a vacuum chamber in fluid communication with the canister; a piston disposed in the vacuum chamber; a pump handle coupled to the piston so as to move the piston in the vacuum chamber between a first position and a second position so as to create the vacuum, the pump handle moving between a retracted position and an extended position, wherein the piston is in the first position when the pump handle is in the retracted position and is in the second position when the pump handle is in the extended position; and a spring disposed in the vacuum chamber for biasing the piston into the second position such that the spring compresses as the piston is moved from the second position to the first position, wherein upon manually pumping the pump handle, the piston creates a vacuum so as to create the vacuum at the wound site and to draw any fluids from the wound site into the canister.

According to another embodiment of the present invention, a portable pump is provided for negative pressure wound therapy for drawing a vacuum from a wound site via a tube, the portable pump comprising: an inlet configured to attach the tube from the wound site; a canister in fluid communication with the inlet for collecting fluids drained from the wound site; and a manually-actuated pump mechanism for creating the vacuum. The manually-actuated pump mechanism comprises: a vacuum chamber in fluid communication with the canister; a piston disposed in the vacuum chamber; and a pump handle coupled to the piston so as to move the piston in the vacuum chamber between a first position and a second position so as to create the vacuum, the pump handle moving between a retracted position and an extended position, wherein the piston is in the first position when the pump handle is in the retracted position and is in the second position when the pump handle is in the extended position, wherein upon manually pumping the pump handle, the piston creates a vacuum so as to create the vacuum at the wound site and to draw any fluids from the wound site into the canister. The portable pump further comprises an automatic lock/release mechanism for selectively locking the pump handle in the retracted position and releasing the pump handle such that the piston may be moved into the second position and hence the pump handle is moved into the extended position.

According to another embodiment of the present invention, a portable pump is provided for negative pressure wound therapy for drawing a vacuum from a wound site via a tube, the portable pump comprising: an inlet configured to attach the tube from the wound site; a canister in fluid communication with the inlet for collecting fluids drained from the wound site; a pressure sensor for sensing a pressure level in the canister; a pressure level indicator for indicating the sensed pressure level in the canister; and a manually-actuated pump mechanism for creating the vacuum.

According to another embodiment of the present invention, a portable pump is provided for negative pressure wound therapy for drawing a vacuum from a wound site via a tube, the portable pump comprising: an inlet configured to attach the tube from the wound site; a canister in fluid communication with the inlet for collecting fluids drained from the wound site; a pressure sensor for sensing a pressure level in the canister; a manually-actuated pump mechanism for creating the vacuum; and a controller coupled to the pressure sensor and the pressure selection input mechanism for prompting the user to manually pump the manually-actuated pump mechanism when the sensed pressure level is below the selected target pressure level.

According to another embodiment of the present invention, a portable pump is provided for negative pressure wound therapy for drawing a vacuum from a wound site via a tube, the portable pump comprising: an inlet configured to attach the tube from the wound site; a canister in fluid communication with the inlet for collecting fluids drained from the wound site; a fluid level sensor in the canister for sensing a level of fluid in the canister; an audio alarm; a controller coupled to the fluid level sensor and the audio alarm for causing the audio alarm to generate an alarm when the sensed fluid level reaches a predetermined level; and a manually-actuated pump mechanism for creating the vacuum.

According to another embodiment of the present invention, a portable pump is provided for negative pressure wound therapy for drawing a vacuum from a wound site via a tube, the portable pump comprises: an inlet configured to attach the tube from the wound site; a canister in fluid communication with the inlet for collecting fluids drained from the wound site; and a manually-actuated pump mechanism for creating the vacuum. The manually-actuated pump mechanism comprising: a vacuum chamber in fluid communication with the canister; a piston disposed in the vacuum chamber; and a pump handle coupled to the piston so as to move the piston in the vacuum chamber between a first position and a second position so as to create the vacuum, the pump handle moving between a retracted position and an extended position, wherein the piston is in the first position when the pump handle is in the retracted position and is in the second position when the pump handle is in the extended position, wherein upon manually pumping the pump handle, the piston creates a vacuum so as to create the vacuum at the wound site and to draw any fluids from the wound site into the canister. The portable pump further comprises a check valve disposed between the vacuum chamber and the canister for preventing air from flowing from the vacuum chamber into the canister when the piston is moved from the first position to the second position and for allowing air to be drawn from the canister to the vacuum chamber when the piston is moved from the second position to the first position.

According to another embodiment of the present invention, a portable pump is provided for negative pressure wound therapy for drawing a vacuum from a wound site via a tube, the portable pump comprising: an inlet configured to attach the tube from the wound site; an activation mechanism for a user to activate the portable pump; a canister in fluid communication with the inlet for collecting fluids drained from the wound site; and a manually-actuated pump mechanism for creating the vacuum. The portable pump further comprises a controller configured to sense manipulation of the activation mechanism and to respond to manipulation of the activation mechanism by tracking time during which the portable pump is activated and automatically shutting down the portable pump upon expiration of a predetermined time period after manipulation of the activation mechanism.

These and other features, advantages, and objects of the present invention will be further understood and appreciated by those skilled in the art by reference to the following specification, claims, and appended drawings.

BRIEF DESCRIPTION OF THE DRAWINGS

The present invention will become more fully understood from the detailed description and the accompanying drawings, wherein:

FIG. 26 is an elevational view of the left side of the portable pump shown in FIG. 1 with the activation mechanism in position to render the portable pump inactive and pump handle shown in the retracted position;

FIG. 27 is an elevational view of the left side of the portable pump shown in FIG. 1 with the activation mechanism in position to render the portable pump active and pump handle shown in the extended position;

DETAILED DESCRIPTION OF THE EMBODIMENTS

Figure 1:
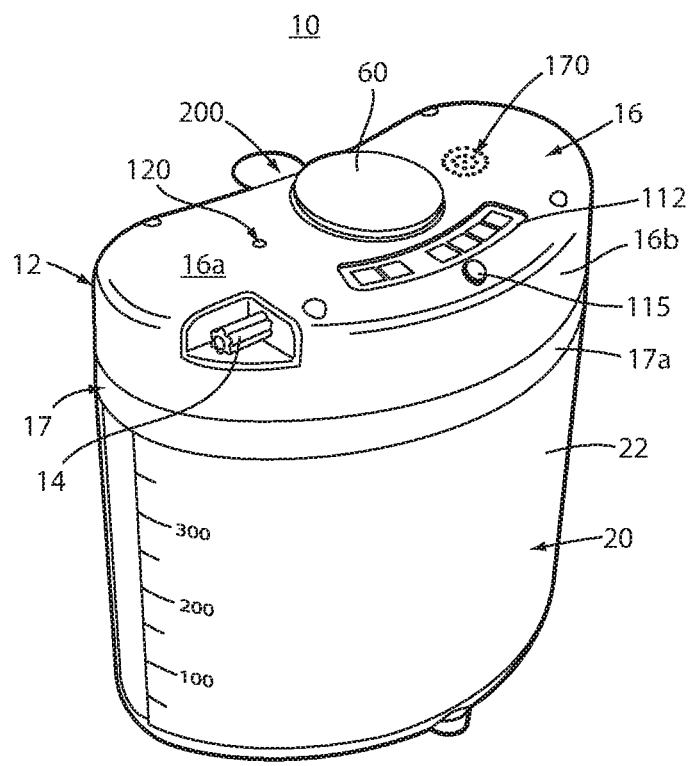
FIG. 1 is a perspective view of a top, front, and left side of a portable pump constructed according to one embodiment.

For purposes of description herein the terms "top," "bottom," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to the embodiment illustrated in FIGS. 1-33, reference numeral 10 generally designates a portable pump that may be used for negative pressure wound therapy. In negative wound therapy, a pump is used to draw a vacuum from a wound site via a tube. The wound site may be wrapped in a drape having an opening in which a connector is provided in known fashion. The tube connects to the connector and acts as a conduit between the connector and the pump. The particular manner in which a wound may be dressed for purposes of negative pressure wound therapy is known in the art and is not otherwise described herein.

Figure 7:
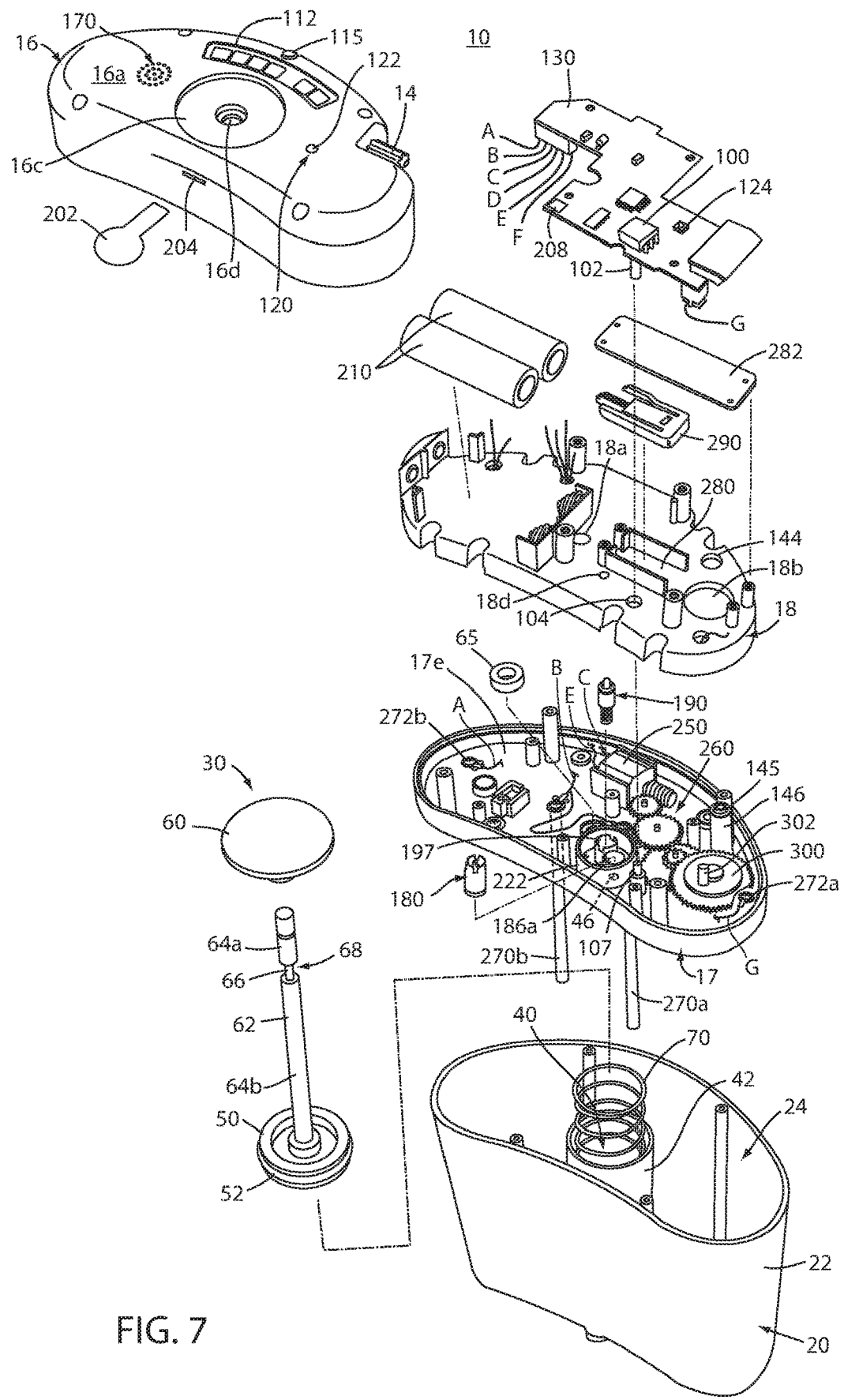
FIG. 7 is an exploded perspective view of the top, rear, and left side of the portable pump shown in FIG. 1.
Figure 11:
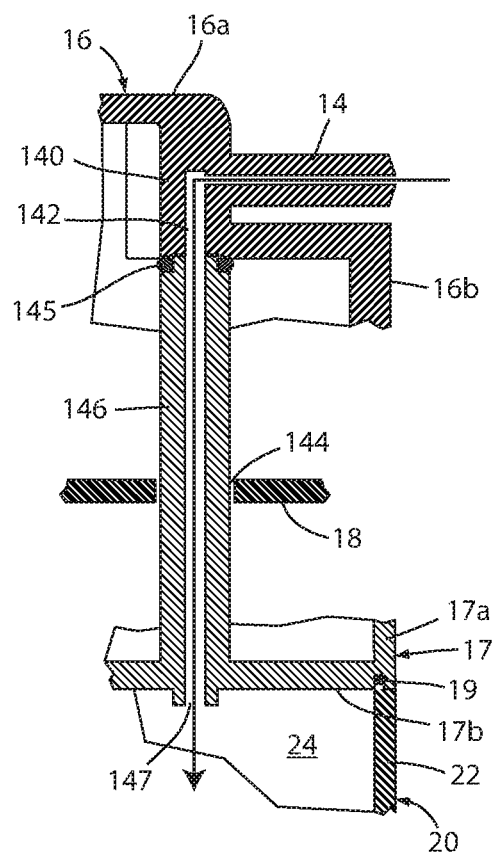
FIG. 11 is an enlarged cross-sectional view of the inlet and connecting portions taken along line XI-XI in FIG. 10.
Figure 12:
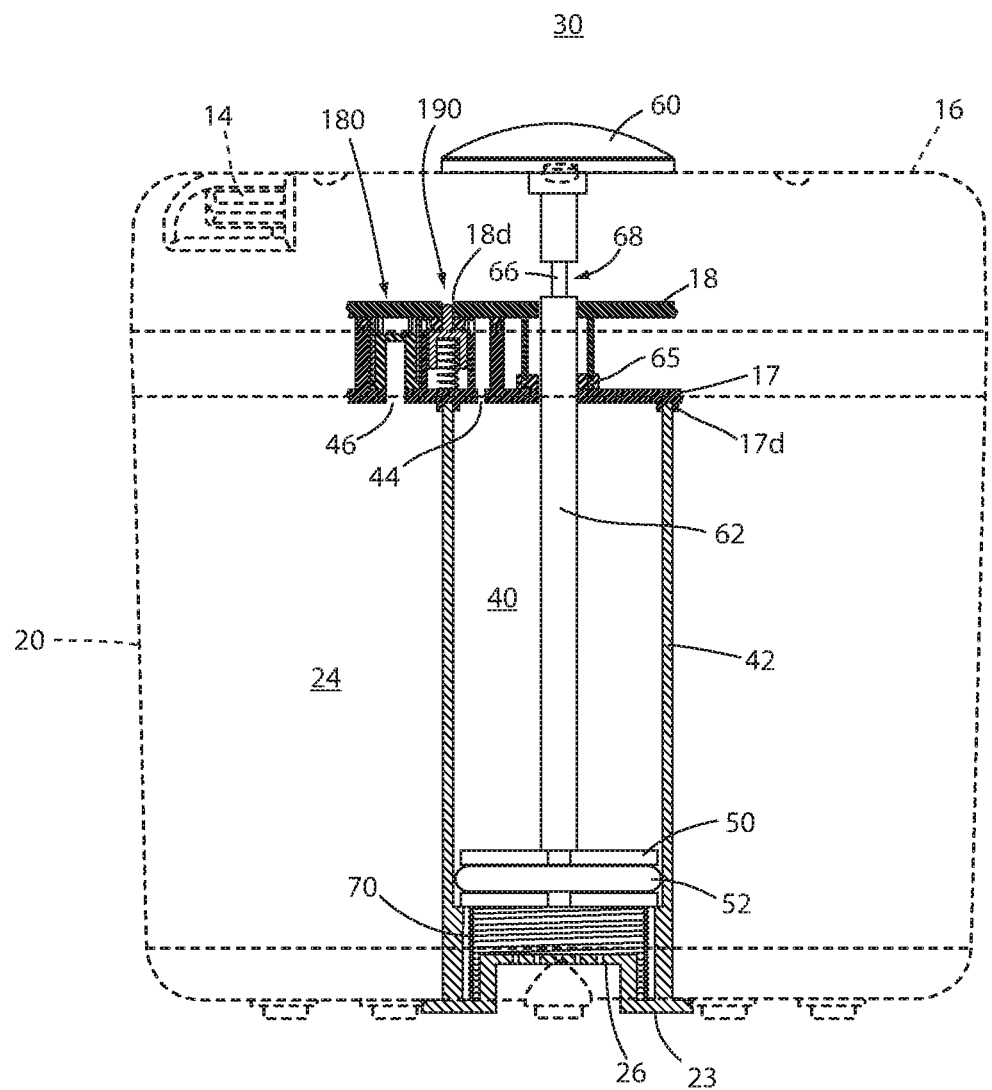
FIG. 12 is a partial cross-sectional view of a manually-actuated pump mechanism used in the portable pump shown in FIG. 1 with a pump handle shown in a retracted position and a piston shown in a first position.
Figure 13:
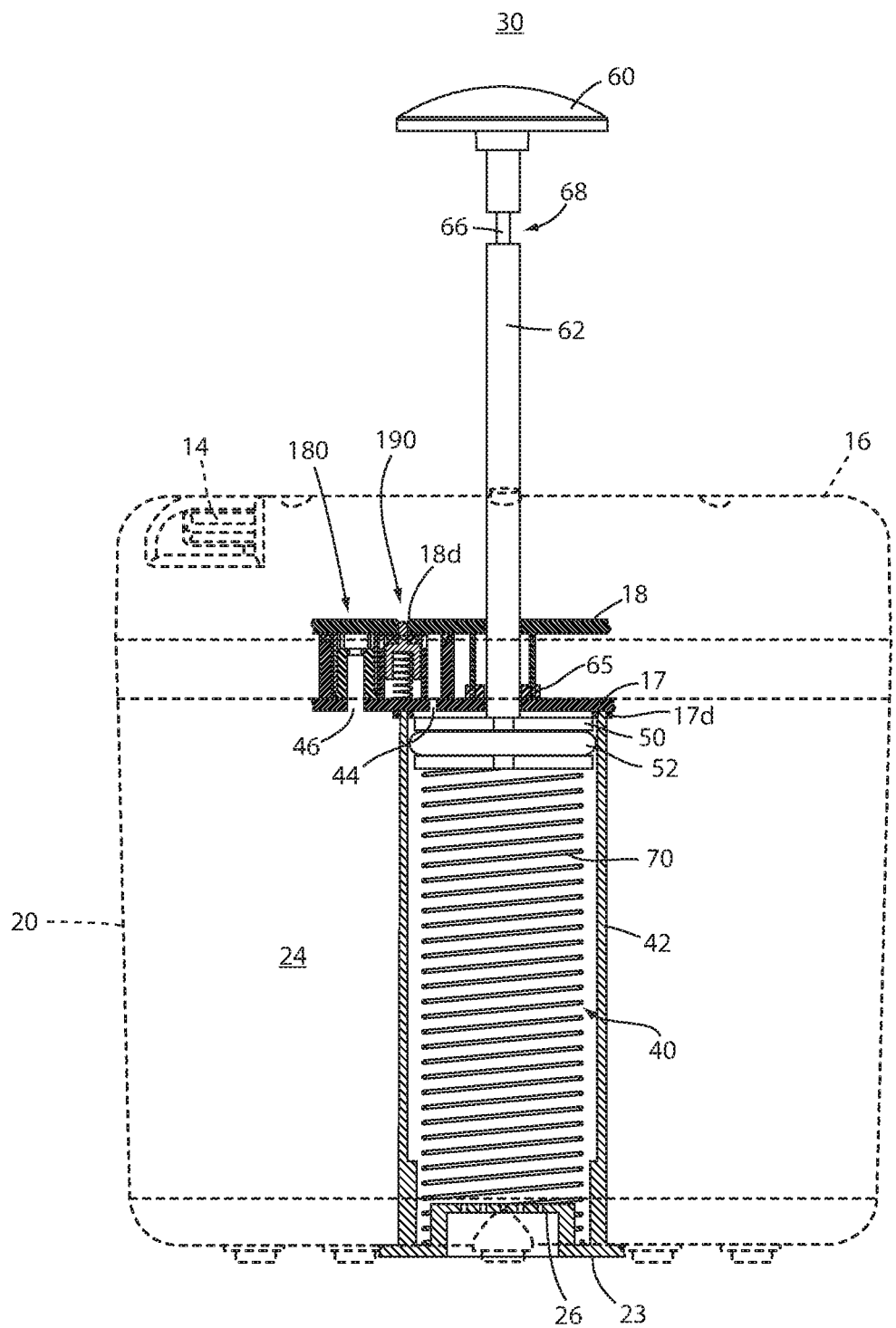
FIG. 13 is a partial cross-sectional view of a manually-actuated pump mechanism used in the portable pump shown in FIG. 1 with a pump handle shown in an extended position and a piston shown in a second position.

As best shown in FIGS. 1-9, portable pump 10 includes a housing 12, an inlet 14 accessible from an outside of housing 12 and configured to attach the tube from the wound site, a canister 20 in fluid communication with inlet 14 (FIGS. 10 and 11) for collecting fluids drained from the wound site, and a manually-actuated pump mechanism 30 (FIGS. 7, 12, and 13 disposed in housing 12 and canister 20 for creating the vacuum. Manually-actuated pump mechanism 30 includes a vacuum chamber 40 in fluid communication with canister 20, a piston 50 disposed in vacuum chamber 40, and a pump handle 60 coupled to piston 50 via a shaft 62 so as to move piston 50 in vacuum chamber 40 between a first position (FIG. 12) and a second position (FIG. 13) so as to create the vacuum. Pump handle 60 moves between a retracted position (FIG. 12) and an extended position (FIG. 13) wherein piston 50 is in the first position when pump handle 60 is in the retracted position and is in the second position when pump handle 60 is in the extended position. Upon manually pumping pump handle 60, piston 50 creates a vacuum so as to create a negative pressure at the wound site and to draw any fluids from the wound site into canister 20. A gelling agent may be provided in canister 20 to cause the collected fluids to gel within canister 20. This causes the fluid to turn into a semi-solid to minimize movement of the fluid within canister 20. The gelling agent may be provided in form of a gel pack.

As shown in FIGS. 12 and 13, manually-actuated pump mechanism 30 may further include a spring 70 disposed in vacuum chamber 40 for biasing piston 50 into the second position such that spring 70 compresses as piston 50 is moved from the second position to the first position.

As described further below with respect to FIGS. 19-25, portable pump 10 may further include an automatic lock/release mechanism 80 for selectively locking pump handle 60 in the retracted position and releasing pump handle 60 such that piston 50 may be moved into the second position and hence pump handle 60 is moved into the extended position.

Figure 2:
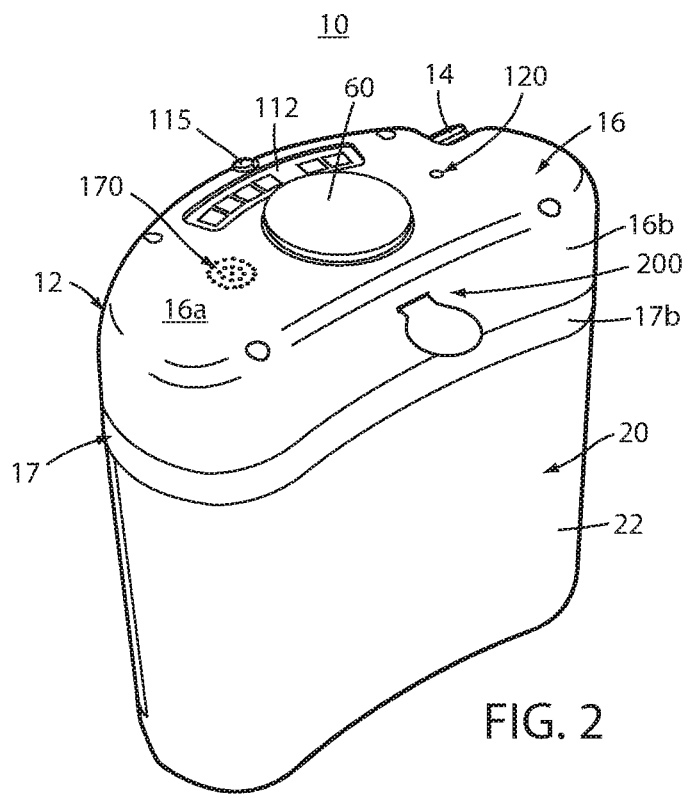
FIG. 2 is a perspective view of the top, rear, and right side of the portable pump shown in FIG. 1.
Figure 3:
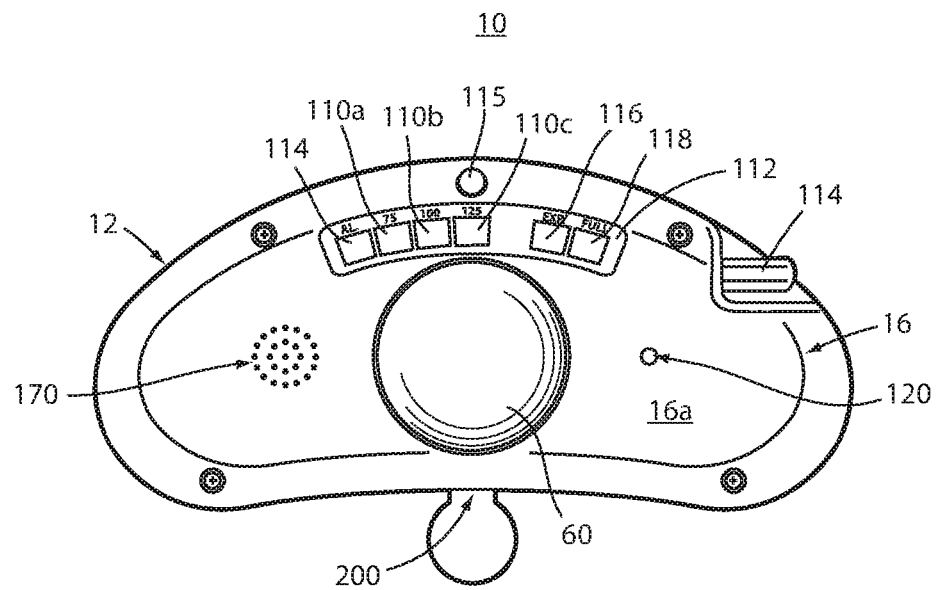
FIG. 3 is a plan view of the top of the portable pump shown in FIG. 1.

As described further below with respect to FIGS. 7 and 32, portable pump 10 may further include a pressure sensor 100 for sensing a pressure level in canister 20. Also, as shown in FIGS. 2 and 3, portable pump 10 may include an indicator light panel including pressure level indicator lights 110a-110c on housing 12 for indicating the sensed pressure level in canister 20 or elsewhere within portable pump 10 so as to indicate the pressure at the wound site. Portable pump may also include a pressure selection input mechanism 120 for allowing a target pressure level to be selected from one of a plurality of different target pressure levels, and a controller 150 coupled to pressure sensor 100 and pressure selection input mechanism 120 for prompting the user to manually pump the pump handle 60 when the sensed pressure level is below the selected target pressure level. Controller 150 (FIG. 32) may also be coupled to pressure level indicator lights 110a-110c for causing indicator lights 110a-110c to indicate the sensed pressure level.

As described further below with respect to FIGS. 7, 8, and 32, portable pump 10 may further include a fluid level sensor 160 in canister 20 for sensing a level of fluid in canister 20, and an audio alarm 170. Controller 150 may be coupled to fluid level sensor 160 and audio alarm 170 for causing audio alarm 170 to generate an alarm when the sensed fluid level reaches a predetermined level.

As described further below with respect to FIGS. 12-18, portable pump 10 may further include a check valve 180 disposed between vacuum chamber 40 and canister 20 for preventing air from flowing from vacuum chamber 40 into canister 20 when piston 50 is moved from the first position to the second position while allowing air to be drawn from canister 20 into vacuum chamber 40 when piston 50 is moved from the second position to the first position.

Further, as described further below with respect to FIGS. 26-32, portable pump 10 may include an activation mechanism 200 for a user to activate portable pump 10. Controller 150 may be configured to sense manipulation of activation mechanism 200 and to respond to manipulation of activation mechanism 200 by tracking time during which portable pump 10 is activated and automatically shutting down portable pump 10 upon expiration of a predetermined time period after manipulation of activation mechanism 200.

Referring back to FIGS. 1-8, housing 12 of portable pump 10 may include an upper shell 16 whose top surface 16a forms the top of pump 10 and a lower shell 17 that includes a peripheral wall 17a that extends between a peripheral wall 16b of upper shell 16 and the vertical walls 22 of canister 20. As best shown in FIGS. 8 and 11, an O-ring seal 19 is provided between lower shell 17 and canister 20 so as to prevent the contents of canister 20 from leaking outside of housing 12 and canister 20. A groove (FIG. 11) may be provided in the bottom surface of lower shell 17 or in the top edge of the vertical walls 22 of canister 20 or in both to engage the seal 19 and hold it in place.

As shown in FIGS. 1-8 and 32, a status input pushbutton 115 may also be provided that is coupled to controller 150, which responds to actuation of pushbutton 115 by illuminating one or more of the indicator lights in indicator light panel 112. This may include illuminating a particular one of pressure indicator lights 110*a*-110*c* to display the target pressure level to which portable pump 10 has been set through use of pressure selection input mechanism 120, or it may display the pressure in canister 20 as sensed by the pressure sensor 100.

Figure 4:
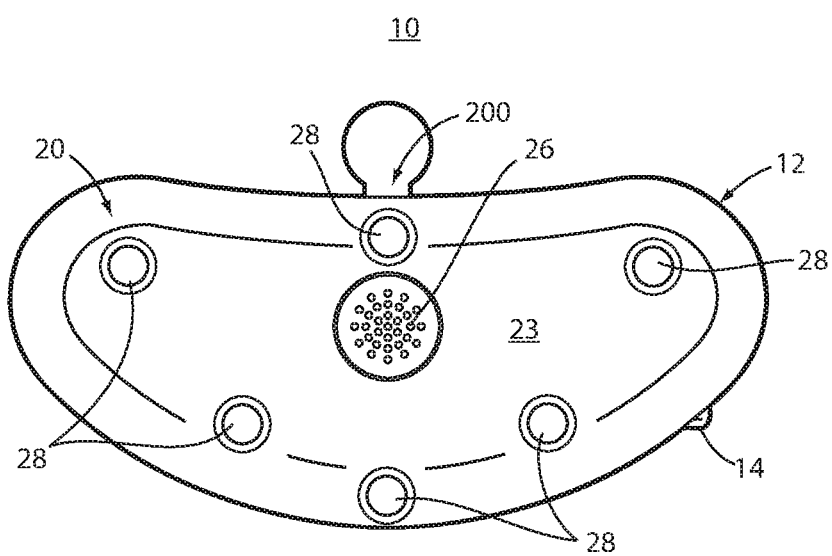
FIG. 4 is a plan view of the bottom of the portable pump shown in FIG. 1.
Figure 5:
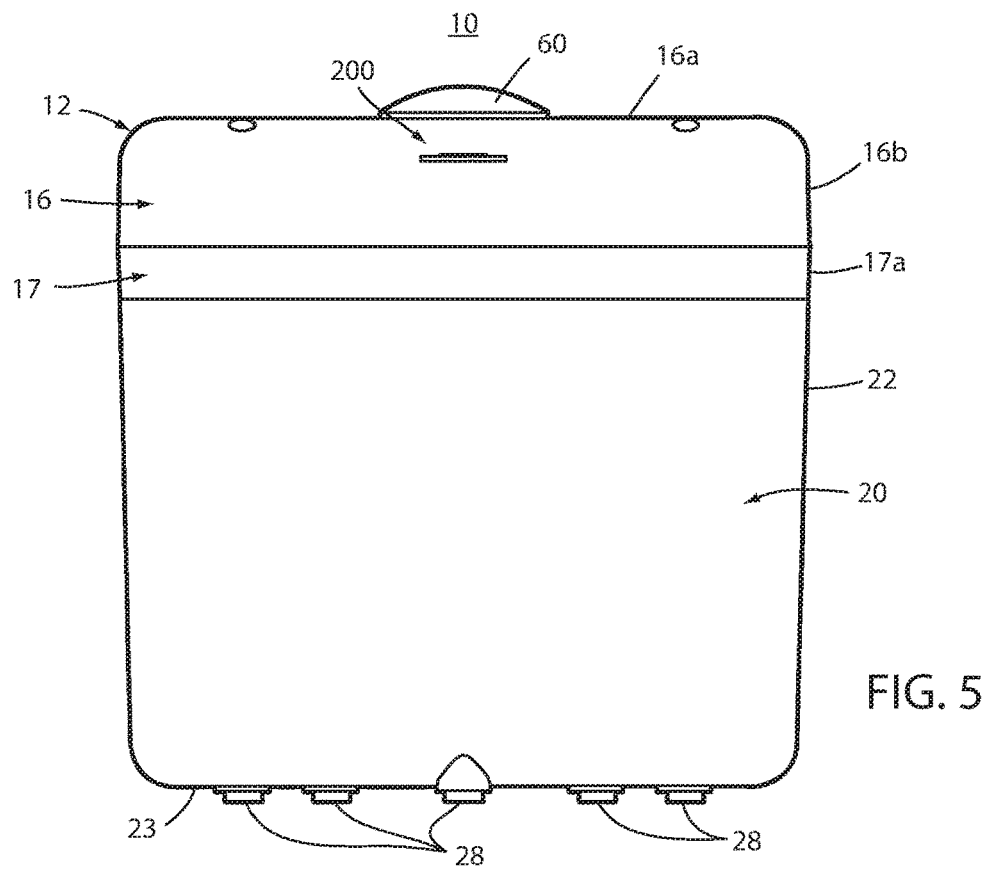
FIG. 5 is an elevational view of the rear of the portable pump shown in FIG. 1.
Figure 6:
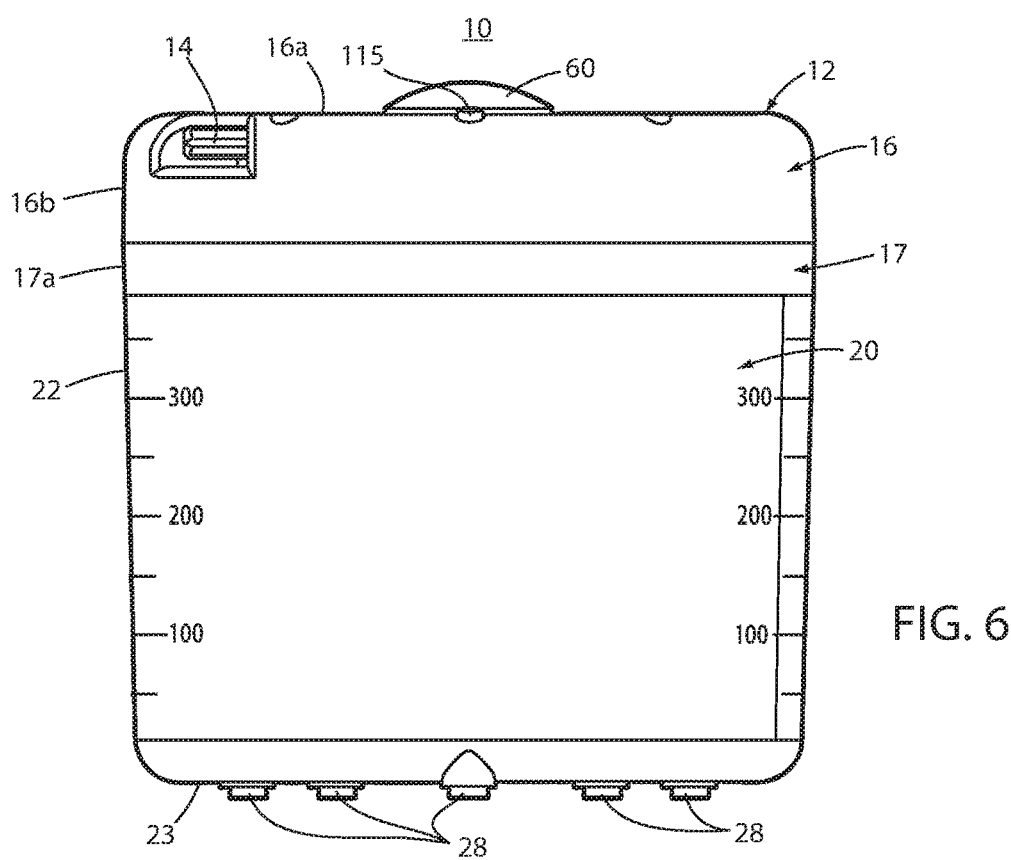
FIG. 6 is an elevational view of the front of the portable pump shown in FIG. 1.

With reference to FIG. 4, the bottom surface 23 of canister 20 is shown. A plurality of feet 28 may be provided around bottom surface 23 to provide a stable base on which portable pump 10 may be set. As discussed further below, a vent 26 may be disposed in the bottom surface 23 so as to allow air to flow into and out of vacuum chamber 40 on the underside of piston 50.

Figure 32:
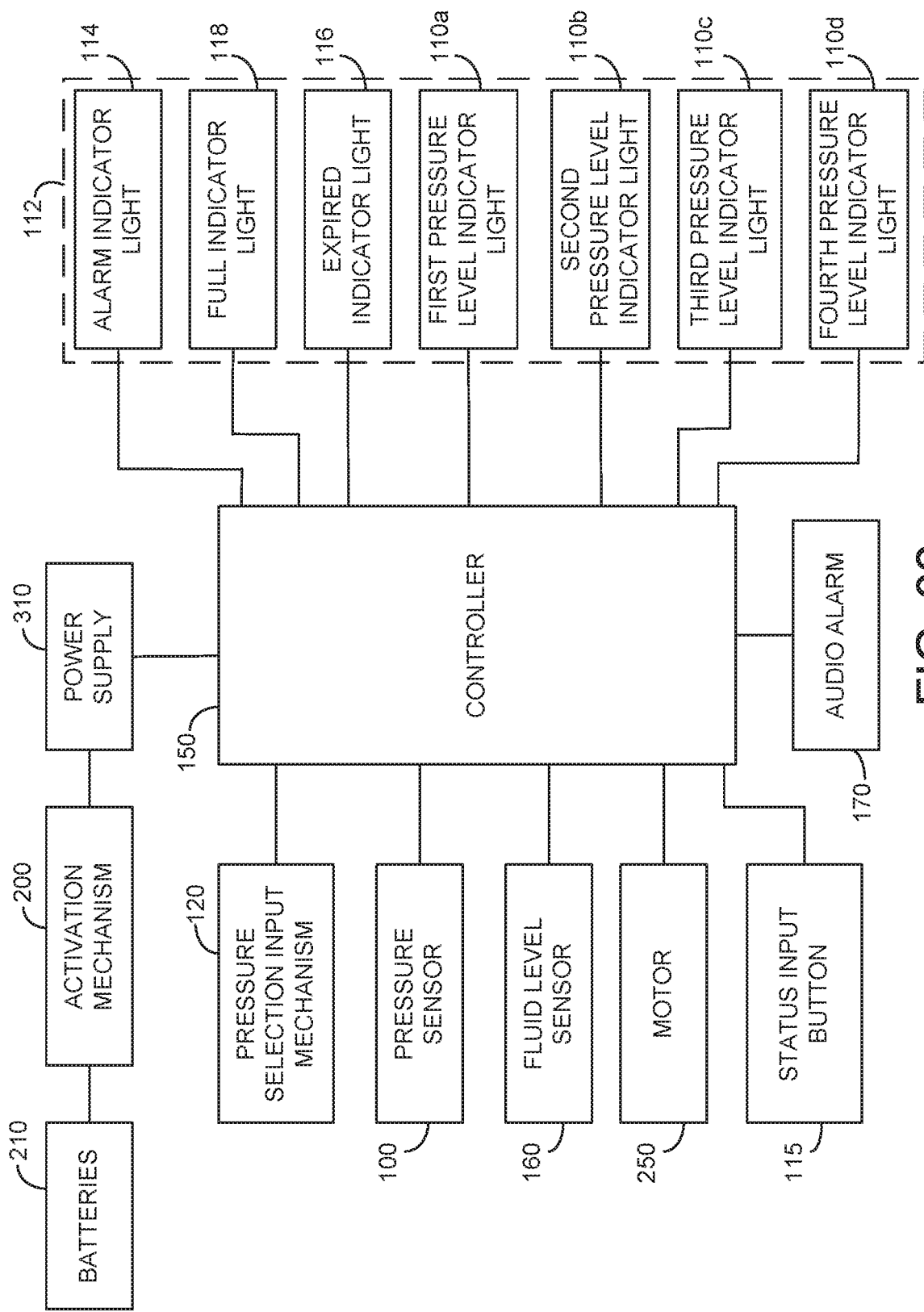
FIG. 32 is an electrical circuit diagram in block form of the electrical circuit components of the portable pump shown in FIG. 1.

As shown in FIGS. 3 and 32, indicator light panel 112 may include not only pressure level indicator lights 110*a*-110*c*, but it may also include an alarm indicator light 114, which is illuminated when an alarm condition occurs. Further, panel 112 may include an expiration indicator light 116, which is illuminated upon expiration of the life of portable pump 10. Further, indicator light panel 112 may include a full indicator light 118, which indicates when canister 20 is full of fluid as sensed using fluid level sensor 160.

Figure 8:
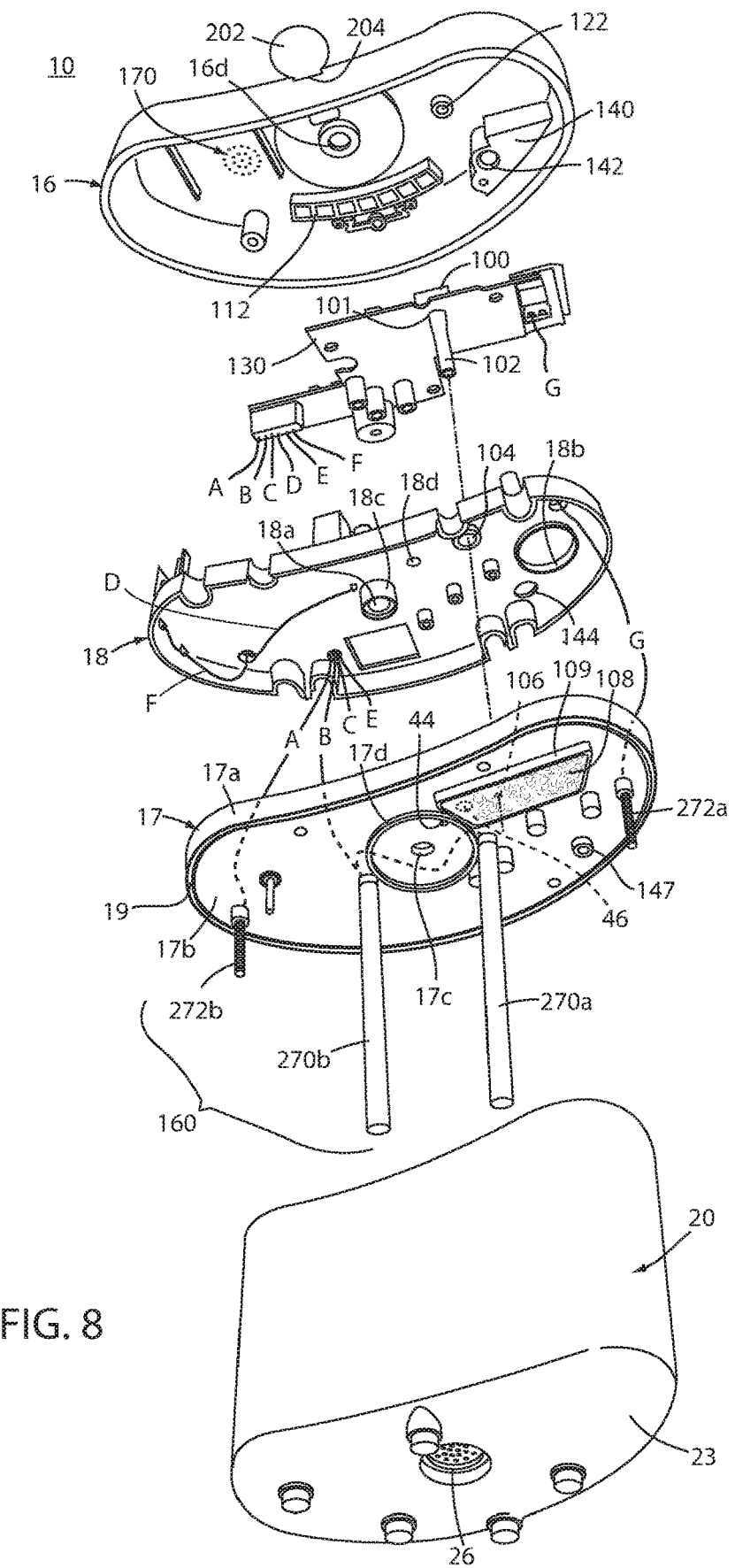
FIG. 8 is an exploded perspective view of the bottom, rear, and left side of the portable pump shown in FIG. 1.

Reference is now made to FIGS. 7 and 8, which show various internal components of portable pump 10. As illustrated, upper shell 16 and lower shell 17 join together to form a cavity therebetween in which various mechanical and electrical components are provided. Further, an internal support member 18 may be provided within the cavity between shells 16 and 17. Internal support member 18 provides a location and appropriate terminals for placement of one or more batteries 210, which are used to power portable pump 10. Further, internal support member 18 provides a location for mounting a circuit board 130 on which the electrical components shown in FIGS. 32 and 24 may be mounted. In addition, a pocket 280 (FIG. 7) is provided for receipt of an actuator 290, which forms part of automatic lock/release mechanism 80. Pocket 280 may be closed at its top by a plate 282. As described further below, actuator 290 is moved linearly within pocket 280 by a drive wheel 300, which in turn is driven by a motor 250 via a gear drive train 260. This drive mechanism is described further below with respect to FIG. 19. Motor 250 is operated under control of controller 150 (FIG. 32). The motor 250 and gear drive train 260 are disposed between lower shell 17 and internal support member 18. Drive wheel 300 extends up through a hole 18*b* in internal support member 18.

As discussed above, portable pump 10 may include fluid sensor 160. Fluid sensor 160 may be implemented using electrically conductive ground posts 270*a* and 270*b* (FIG. 8) as well as two shorter electrically conductive pins 272*a* and 272*b*, which may be in the form of screws or bolts. As shown, pins 272*a* and 272*b* do not extend very far below the lower surface 17*b* of lower shell 17 relative to ground pins 270*a* and 270*b*. In this manner when the fluid level is below the ends of pins 272*a*-272*b*, controller 150 will not sense any current flow between ground pins 270*a* and 270*b* and pins 272*a* and 272*b*. However, when the fluid rises to a point where the ends of pins 272*a* and 272*b* extend below the surface of the fluid, current may flow through the fluid between pins 272*a* and 272*b* and pins 270*a* and 270*b*. Upon detecting this flow of current, controller 150 may determine that the canister 20 is full of fluid whereby the controller 150 may take appropriate action as discussed further below.

As also mentioned above, portable pump 10 may include a pressure selection input mechanism 120. Such a mechanism may be provided in the form of a pushbutton switch provided on an outer surface of housing 12 or provided on circuit board 130 in the form of a pushbutton switch 124 (see FIG. 7) that is positioned directly below an aperture 122 through the upper surface 16*a* of upper shell 16. This allows a person to insert a pin through hole 122 to activate pushbutton switch 124. Switch 124 may be coupled to controller 150 (FIG. 32) so as to toggle between a plurality of selectable target pressure levels. For example, such target pressure levels may include target pressures of 75, 100, 125, and 150 mm of Hg. With each activation of switch 124, controller 150 may illuminate a respective one of pressure level indicator lights 110*a*, 110*b*, or 110*c* (or optionally 110*d* (FIG. 32)) to provide feedback for the user to confirm the selected target pressure level. As discussed further below, the target pressure level may be obtained by prompting the user to manipulate pump handle 60 until such point that a pressure sensor 100 senses that the pressure within canister 20 has reached the target pressure level. The pressure sensor 100 is shown in FIGS. 7 and 8. As illustrated, pressure sensor 100 is mounted on a top surface of circuit board 130. A tube 102 may pass through an aperture 101 in circuit board 130 so as to join the pressure sensor 100. Tube 102 extends through an aperture 104 in internal support member 18 and connects to a hollow post 107 that extends upward from the upper surface 17*e* of lower shell 17. Hollow post 107 in turn has a port 106 opening through lower shell 17 so as to allow pressure sensor 100 to sense the pressure within the interior 24 of canister 20. As shown in FIG. 8, port 106 as well as a port 46 (described below) may be covered by a foam pad 108 that is held against the lower surface 17*b* of lower shell 17 by a retaining wall 109 that extends around the periphery of pad 108. Pad 108 prevents fluid from splashing and being drawn through ports 46 and 106.

Audible alarm 170 may be provided through the use of a piezoelectric speaker mounted on circuit board 130 in proximity to a pattern of apertures formed through the upper surface 16*a* of upper shell 16. Alarm 170 is connected to controller 150 (FIG. 32), which controls the activation of alarm 170.

Figure 9:
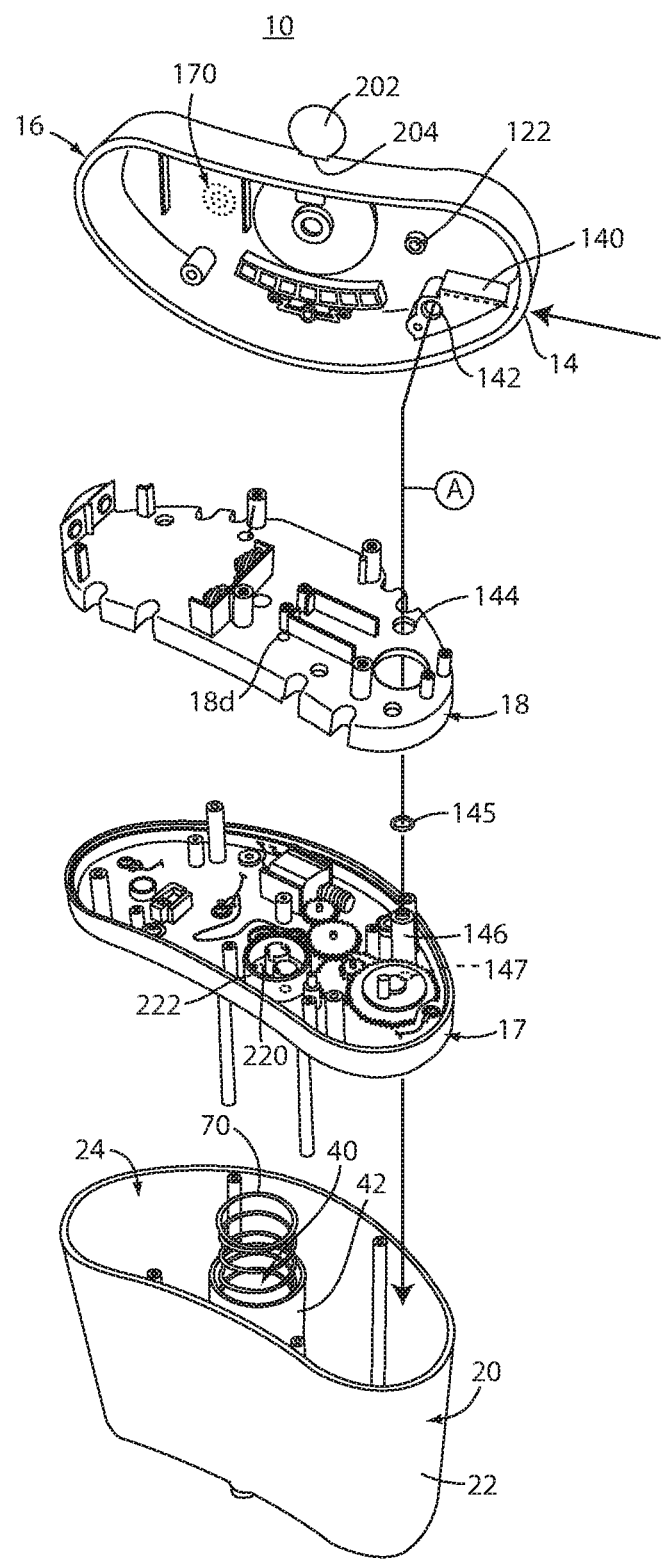
FIG. 9 is another exploded perspective view of the bottom, rear, and left side of the portable pump shown in FIG. 1 to show the flow path of the vacuum through an inlet and into an interior of a canister.
Figure 10:
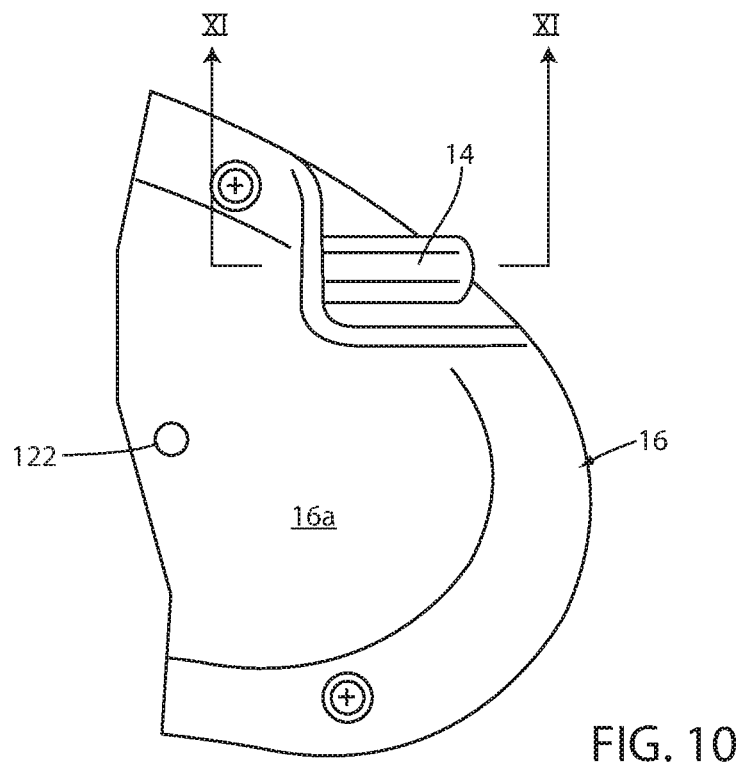
FIG. 10 is an enlarged plan view of a portion of the top of the portable pump as shown in FIGS. 1 and 3.

With reference to FIG. 9, the flow path A, through which air and fluid from the wound are drawn, will now be described. As shown, fluid is first drawn into inlet 14, which protrudes outward from upper shell 16 and is in fluid communication with a conduit 140 having a port 142 on the bottom surface of upper shell 16. As shown in FIGS. 9-11, lower shell 17 may include a hollow post 146 with an opening 147 on the bottom surface 17*b* of lower shell 17. The upper end of hollow post 146 extends through an aperture 144 in internal support member 18 and abuts port 142 where an O-ring 145 may be provided to ensure that the fluid path is sealed whereby air and fluid drawn from the wound site enters inlet 14 and passes through conduit 140 and through hollow post 146 where it exits through opening 147 into the interior 24 of canister 20. As described further below, the vacuum and flow of fluid into canister 20 occurs through the creation of a vacuum within canister 20 by means of the vacuum created in vacuum chamber 40.

Having described the path of fluid flow from inlet 14 to the interior 24 of canister 20, the manner in which the vacuum is created in vacuum chamber 40 and is translated to the interior 24 of canister 20 is now described with reference to FIGS. 7, 8, and 12-18. In particular, a port 44 is provided through lower shell 17 in the region bounded by circular groove 17*d* so as to be in fluid communication with vacuum chamber 40. Further, a port 46 is provided through lower shell 17 so as to be in fluid communication with the interior 24 of canister 22. Both ports 44 and 46 are in fluid communication with an upper chamber 220 (best shown in FIGS. 9 and 16) that is provided between lower shell 17 and internal support member 18. Upper chamber 220 is bounded by cylindrical walls 222 that extend upward from lower shell 17. Cylindrical wall 222 includes a groove 224 at its upper edge for receiving an O-ring gasket 225 (FIGS. 17 and 18), which seals upper chamber 220 against the lower surface of internal support member 18. Also in fluid communication with upper chamber 220 is a port 18*d* extending through internal support member 18. As discussed further below, port 18*d* serves as a pressure relief vent of a pressure relief valve 190.

Figure 14:
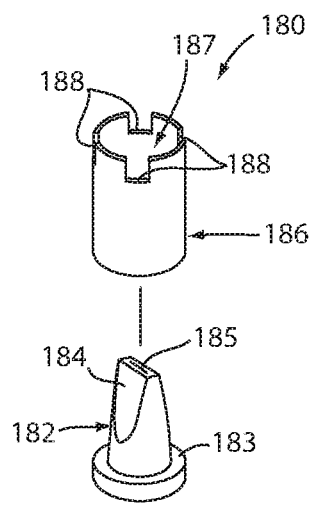
FIG. 14 is an exploded perspective view of a check valve forming part of the manually-actuated pump mechanism shown in FIG. 13.
Figure 18:
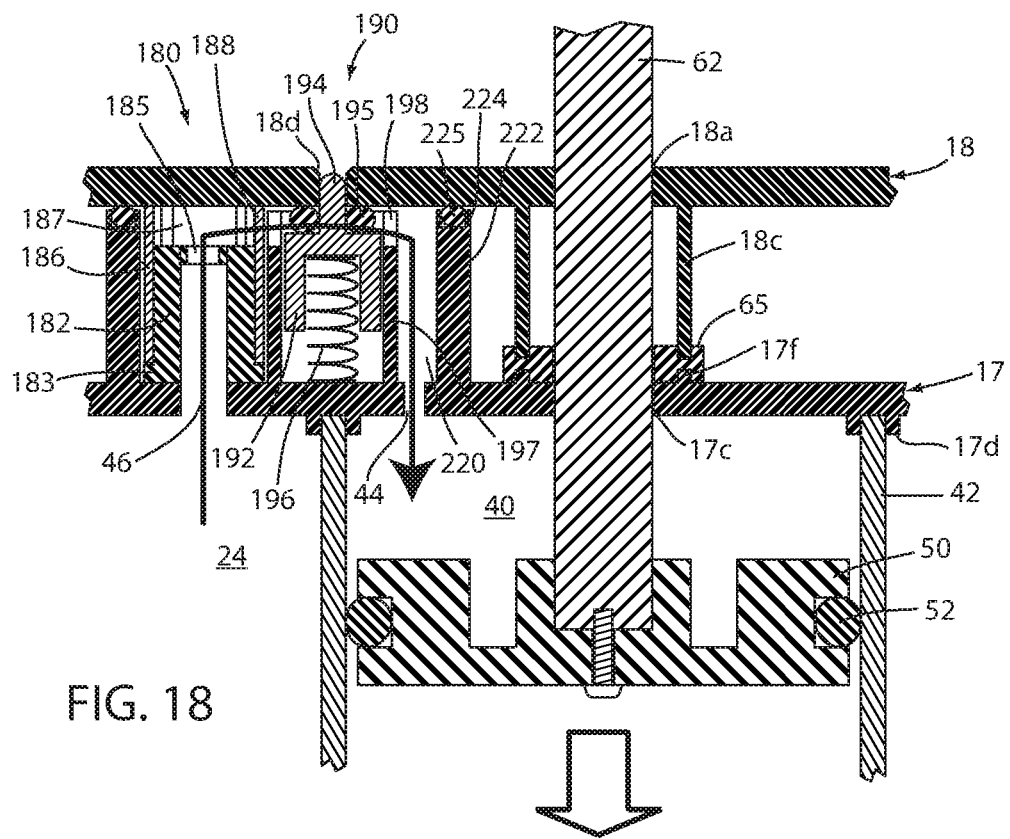
FIG. 18 is an enlarged partial cross-sectional view taken along line XVII-XVII in FIG. 16 showing operation of the check valve and the pressure relief valve as the piston moves from the second position back to the first position.

Within upper chamber 220 are formed two cylindrical volumes confined by cylinders 197 and 186, respectively. Cylinder 197 includes openings 198 at an upper end thereof for allowing air to flow through the walls of cylinder 197. Likewise, cylinder 186 includes apertures 188 also at an upper end thereof for allowing air to flow through the walls of cylinder 186. As mentioned above, a check valve 180 is provided to prevent air from flowing in the wrong direction between the interior 24 of canister 20 and a vacuum chamber 40. As best shown in FIG. 14, check valve 180 includes cylinder 186 which defines a cylindrical volume 187 in which a duck-bill valve component 182 is provided. Duck-bill valve component 182 includes a round flange 183 at the lower end for resting within a well 186*a* (FIG. 16) formed in lower shell 70. An aperture provided through flange 183 communicates with port 46 and provides a flow path through the inside of a tapered end 184 and through a small slit 185 at the end of duck-bill valve component 182. With this particular design, air may be drawn upward through port 46, through the opening in flange 183, out of opening 185, through openings 188 into upper chamber 220, and then through port 44 into vacuum chamber 40 as piston 50 is pumped downward. However, duck-bill valve component 182 does not permit air to flow in the opposite direction as the increased pressure within upper chamber 220 presses opening 185 closed. Thus, as best shown in FIG. 18, as piston 50 is pushed downward in vacuum chamber 40, a vacuum is created in vacuum chamber 40 that causes air to be drawn from canister 20 through port 46, through duck-bill valve component 182, out its open end 185, and through openings 188 into upper chamber 220. The air is further drawn through port 44 into vacuum chamber 40. In the meantime, on the underside of piston 50, air is pushed downward and through vent 26 provided in the bottom 23 of canister 22. On the other hand, as piston 50 is raised by lifting pump handle 60, air within vacuum chamber 40 is pushed back into upper chamber 220 via port 44. This causes the air pressure in upper chamber 220 to build, which forces the opening 185 of duck-bill valve component 182 closed such that air may not flow back into interior 24 of canister 20. As piston 50 is moved upward in chamber 40, air is allowed to enter in vacuum chamber 20 below piston 50 through the vent 26 on the bottom 23 of canister 20.

Figure 15:
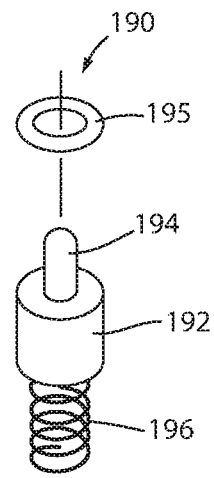
FIG. 15 is an exploded perspective view of a pressure relief valve forming part of the manually-actuated pump mechanism shown in FIG. 13.
Figure 16:
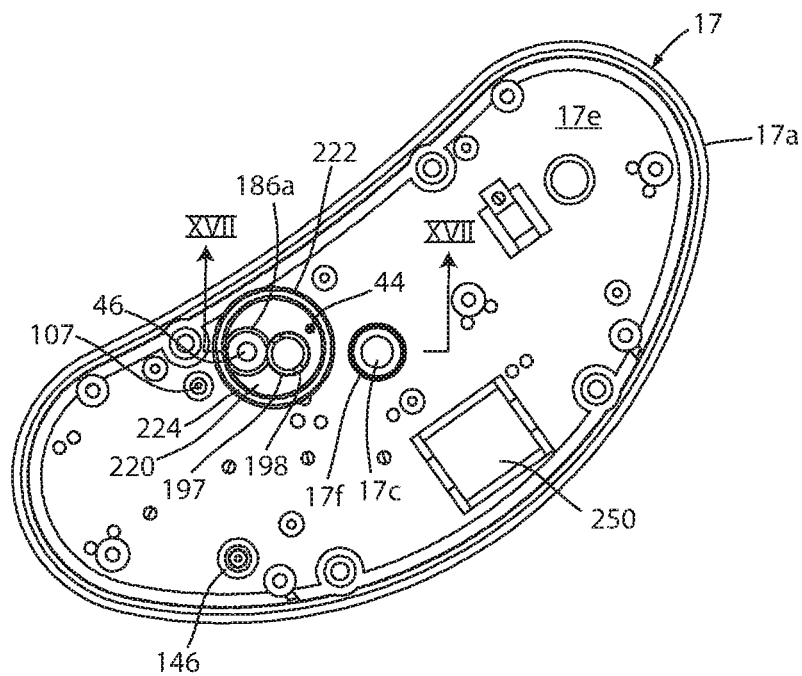
FIG. 16 is a plan view of the bottom of the lower shell used in the portable pump shown in FIG. 1.
Figure 17:
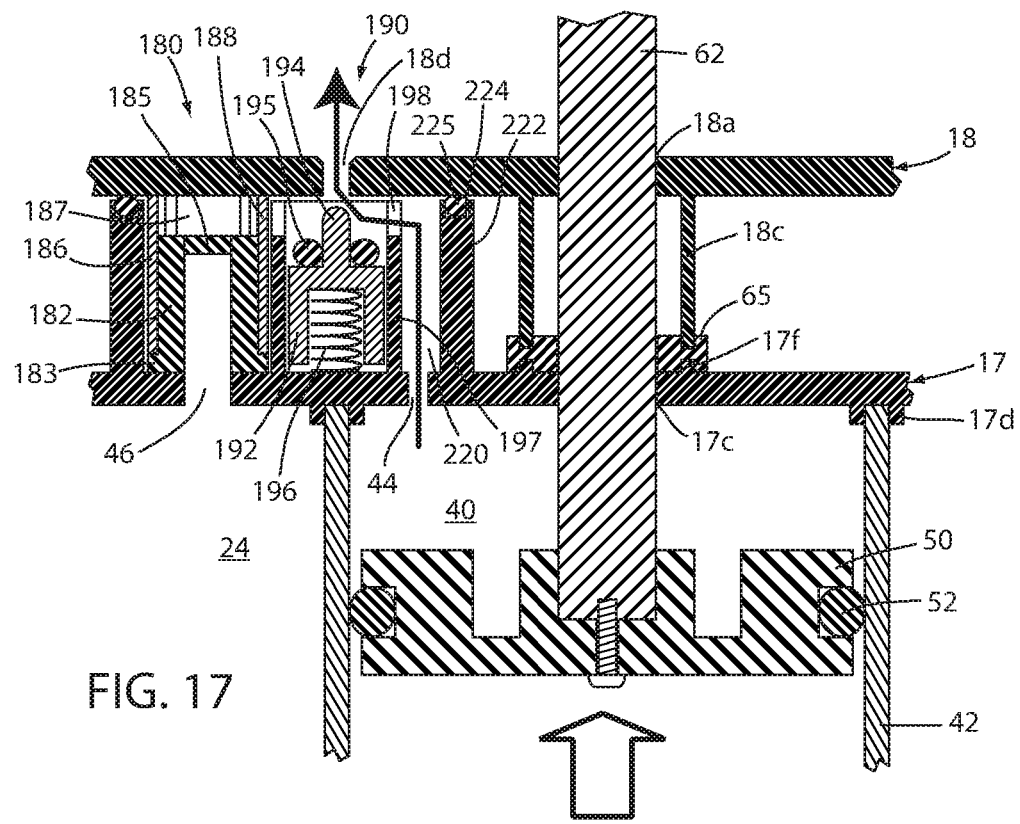
FIG. 17 is an enlarged partial cross-sectional view taken along line XVII-XVII in FIG. 16 showing operation of the check valve and the pressure relief valve as the piston moves from the first position to the second position.

As best shown in FIGS. 15, 17, and 18, pressure relief valve 190 includes a cylindrical body 192 having a nipple 194 on an upper end and an aperture in its bottom for receiving a spring 196. An O-ring 195 may be provided around nipple 194. When the pressure in upper chamber 220 is low, spring 196 pushes nipple 194 upward through port 18*d* in internal support member 18. This prevents air, which is drawn when creating a vacuum through downward movement of piston 50, from being drawn anywhere but from in the inside 24 of canister 20. On the other hand, as shown in FIG. 17, when the pressure in upper chamber 220 builds due to the raising of piston 50 and the closing of check valve 180, the increased pressure causes pressure relief valve 190 to get pushed downward against the bias of spring 196, whereby nipple 194 no longer protrudes through port 18*d* thereby allowing air to flow from within vacuum chamber 40 through port 44, through openings 198 in cylinder 197, and through port 18*d*. Note that a vent hole (not shown) may be provided in upper shell 16 or the side of lower shell 17 to allow this air from port 18*d* to vent to atmosphere.

Having described the flow paths of air/fluid within portable pump 10, manually-actuated pump mechanism 30 will now be described with reference to FIGS. 7, 8, and 17-25. As stated above, manually-actuated pump mechanism 30 includes vacuum chamber 40, piston 50, and pump handle 60 coupled to piston 50 via pump shaft 62. Pump shaft 62 includes an upper portion 64*a* having a first diameter, lower portion 64*b* having a second diameter which may be equal to the first diameter, and a narrowed portion 66 which has a smaller diameter than either the upper or lower portions 64*a* and 64*b*. By providing narrower portion 66 between portions 64*a* and 64*b*, a notch 68 is provided in shaft 62. As discussed further below, notch 68 is provided to allow the automatic lock/release mechanism 80 to lock the pump handle 60 in a retracted position or to release pump handle 60 such that the force of spring 70 pushes the pump handle 60 into an extended position. Piston 50 may be constructed to include a piston ring 52, which is resilient and provides a seal against the inner walls of a cylinder 42 that forms vacuum chamber 40. Cylinder 42 may be integrally molded with the rest of canister 20 and extends upward to fit within a grooved rim 17*d* (FIGS. 8, 12, and 13) formed on the bottom surface of lower shell 17. This is to seal vacuum chamber 40 from direct communication with an interior 24 of canister 20. Vent 26 is provided at the lower end of vacuum chamber 40 so as to allow air to flow into vacuum chamber 40 at the underside of piston 50 as piston 50 is raised upward and then to flow out of vacuum chamber 40 as piston 50 is moved downward. The actual vacuum in canister 20 is created in vacuum chamber 40 above the upper surface of piston 50 as discussed further below. As best shown in FIGS. 12 and 13, spring 70 is compressed by the bottom of piston 50 when piston 50 is in a first position with the pump handle 60 in the retracted position shown in FIG. 12. When pump handle 60 is in the extended position and piston 50 is in the second position, spring 70 is expanded. Spring 70 is configured to push the pump handle 60 into the extended position shown in FIG. 13 when pump handle 60 is not locked and no force is otherwise applied to pump handle 60.

As shown in FIGS. 8, 17, and 18, internal support member 18 may have an aperture 18*a* through which shaft 62 of pump handle 60 may pass. Further, a cylinder 18*c* concentric with aperture 18*a* may extend downward from the bottom surface of internal support member 18 in juxtaposition to a shorter cylinder 17*f* formed on an upper surface of lower shell 17, which is concentric with an aperture 17*c* provided in lower shell 17 through which pump shaft 62 also passes. Cylinders 18*c* and 17*c* cooperate to engage grooves formed in upper and lower surfaces of a gasket 65 which otherwise rests on the upper surface of lower shell 17 and extends around shaft 62 so as to provide a seal against air leakage along the shaft 62. As shown in FIGS. 7 and 8, an aperture 16d may be provided through upper shell 16 which is aligned with apertures 18a and 17c to allow pump shaft 62 to move vertically through these apertures. As best shown in FIG. 12, when the pump handle 60 is in its retracted position, the narrow portion 66 of shaft 62 that provides notch 68 falls within the area between internal support member 18 and upper shell 16 to allow the automatic lock/release mechanism 80 to lock the pump handle 60 in the retracted position (described further below). As shown in FIG. 7, the upper surface 16a of upper shell 16 may include a recess 16c for receiving the pump handle 60 when in the retracted position. This prevents a person from trying to pull upward on the pump handle 60 when it is locked in the retracted position.

Figure 19:
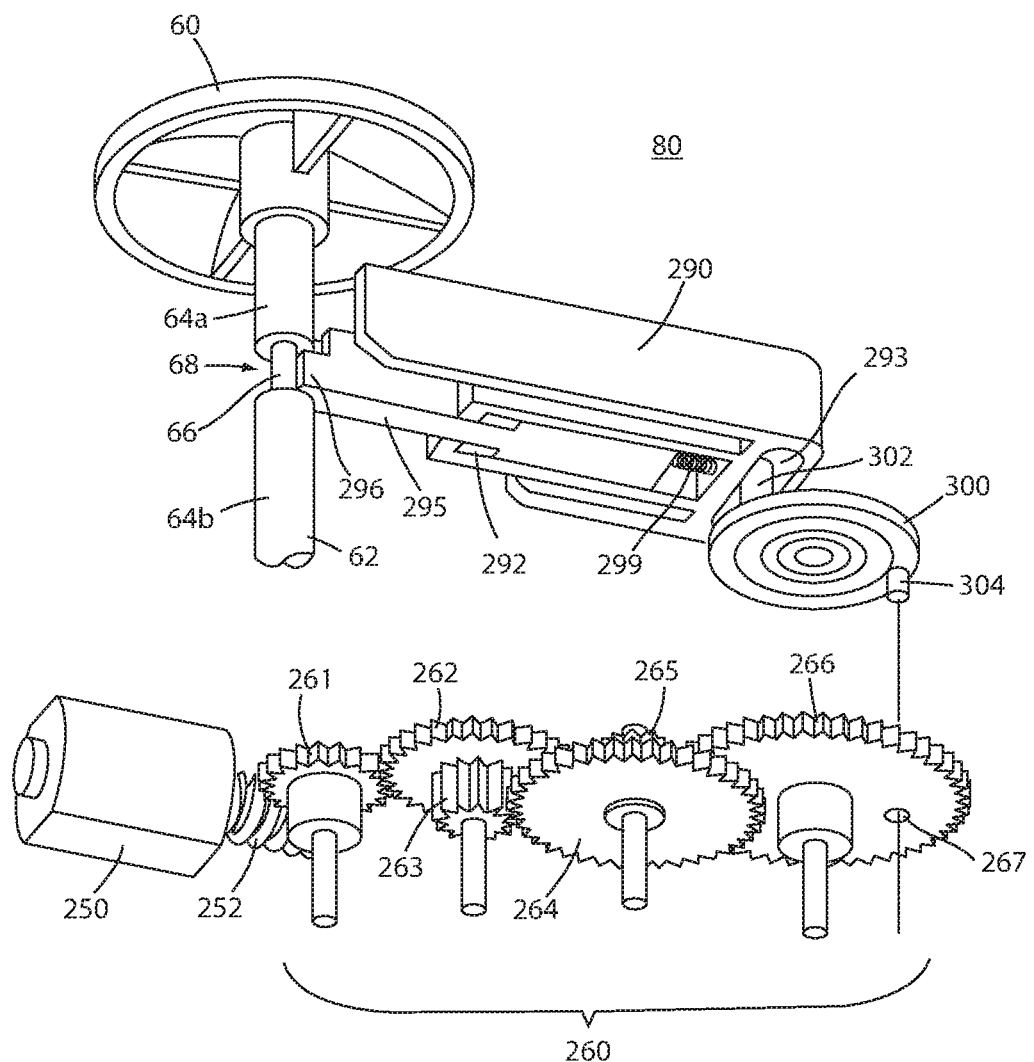
FIG. 19 is an exploded perspective view of an automatic lock/release mechanism that may be used in the portable pump shown in FIG. 1.
Figure 25:
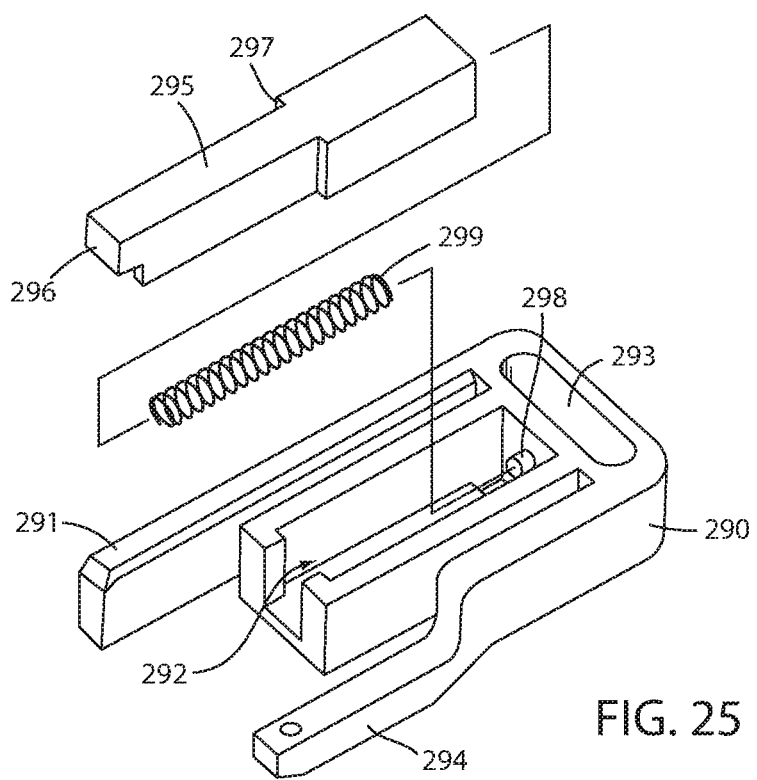
FIG. 25 is an exploded perspective view of the actuator shown in FIG. 24.
Figure 28:
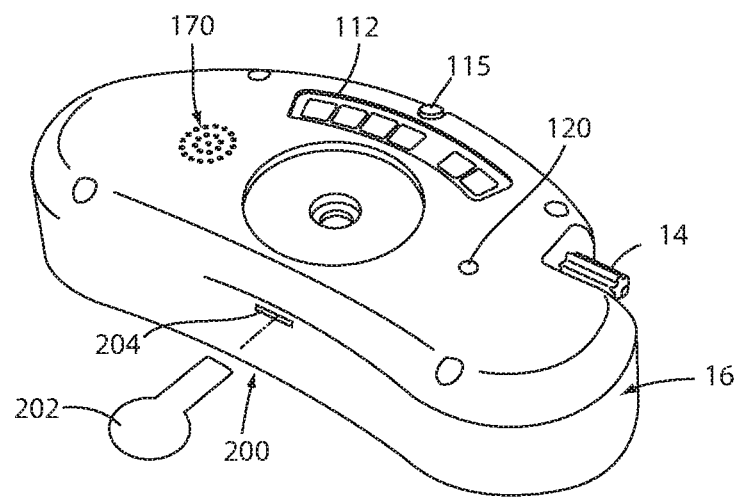
FIG. 28 is a perspective view of the upper shell of the portable pump shown in FIG. 1 with the activation mechanism in position to render the portable pump active.
Figure 29:
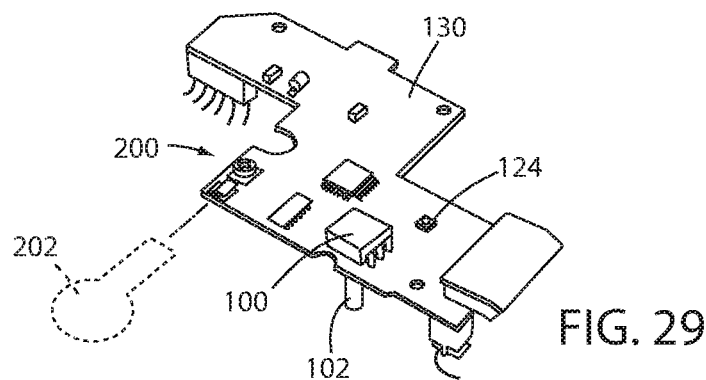
FIG. 29 is a perspective view of the circuit board of the portable pump shown in FIG. 1 with the activation mechanism in position to render the portable pump active.

Automatic lock/release mechanism 80 will now be described with reference to FIGS. 19 25. As shown in FIG. 19, an actuator 290 is shown having a slot 293 formed at one end for receiving an upstanding peg 302 of drive wheel 300. As discussed above with reference to FIG. 7, actuator 290 is constrained by pocket 280, plate 282, and the upper surface of internal support member 18 to move linearly toward or away from pump shaft 62. As described further below, drive wheel 300 rotates in response to actuation of motor 250, which turns a motor screw 252 that engages a gear drive train 260 that in turn rotates drive wheel 300. Rotation of wheel 300 also rotates upstanding peg 302, which, by being provided in an elongated slot 293, causes the rotation of peg 302 to be translated into linear motion of actuator 290 toward and away from pump shaft 62. As shown, gear drive train 260 includes a first gear 261 that directly engages the drive screw 252 of motor 250, a second gear 262 that engages first gear 261 and rotates in response to rotation of first gear 261, and a third gear 263 provided on the same shaft as second gear 262 but having a smaller diameter engages a fourth gear 264. A fifth gear 265 is provided on the same shaft as fourth gear 264 and engages a sixth gear 266. Sixth gear 266 has an aperture 267 for receiving a downward extending peg 304 of drive wheel 300. Thus, rotation of drive screw 252 turns the respective gears through various gearing ratios so as to turn drive wheel 300. Motor 250 may rotate in a single direction or may be reversible.

Figure 24:
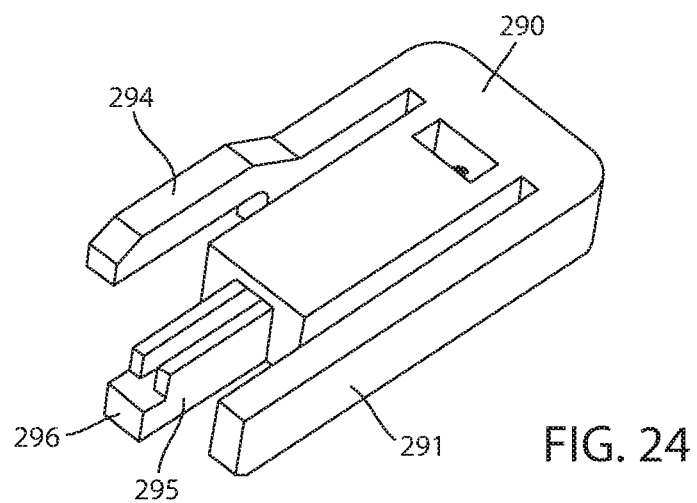
FIG. 24 is a perspective view of the actuator of the automatic lock/release mechanism shown in FIGS. 20-24.

Actuator 290 further includes a rectangular slot 292 for receiving a portion of a latch 295. Rectangular slot 292 includes an aperture at one end through which latch 295 extends toward pump shaft 62. Latch 295 is movable within rectangular slot 292 and is biased towards an extended position by a spring 299 such that a catch 296 at the end of latch 295 is normally biased toward pump shaft 62. As shown in FIG. 25, latch 295 may include a pair of shoulders 297 that prevent latch 295 from moving entirely forward through the opening in rectangular slot 292 and that limit the extended position of latch 295 relative to actuator 290. As shown in FIGS. 24 and 25, actuator 290 may include two side arms 291 and 294 that engage the walls of pocket 280 and/or the lower surface of plate 282 (FIG. 7). Having described the components of automatic lock/release mechanism 80, the operation thereof will now be described.

Figure 20:
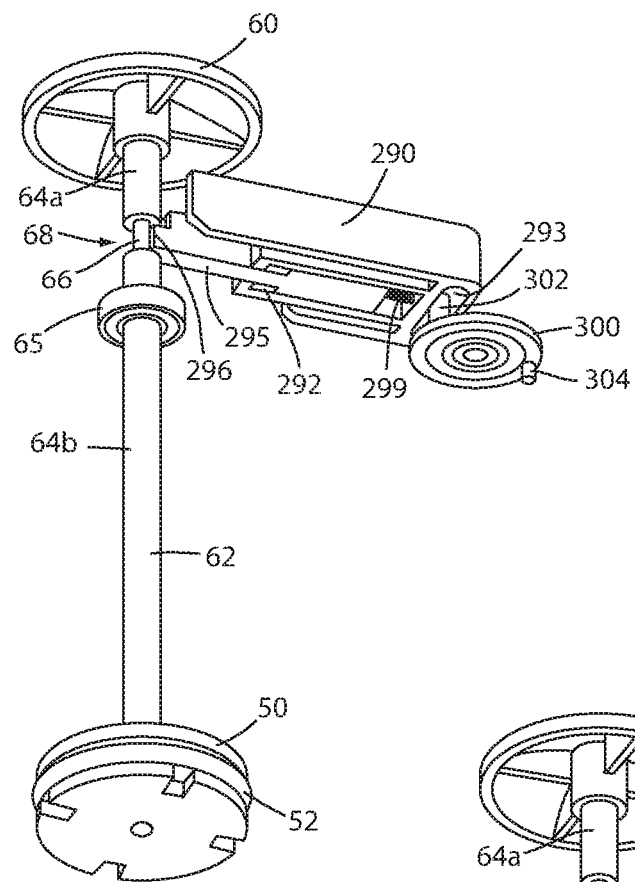
FIG. 20 is a perspective view of the relative position of the automatic lock/release mechanism when the pump handle is locked in the retracted position.

FIG. 20 shows the automatic lock/release mechanism in a locked position. Specifically, actuator 290 is extended toward pump shaft 62 such that catch 296 at the distal end of latch 295 engages notch 68 in pump shaft 62. This prevents upward movement of pump handle 60 and hence any movement of piston 50.

Figure 21:
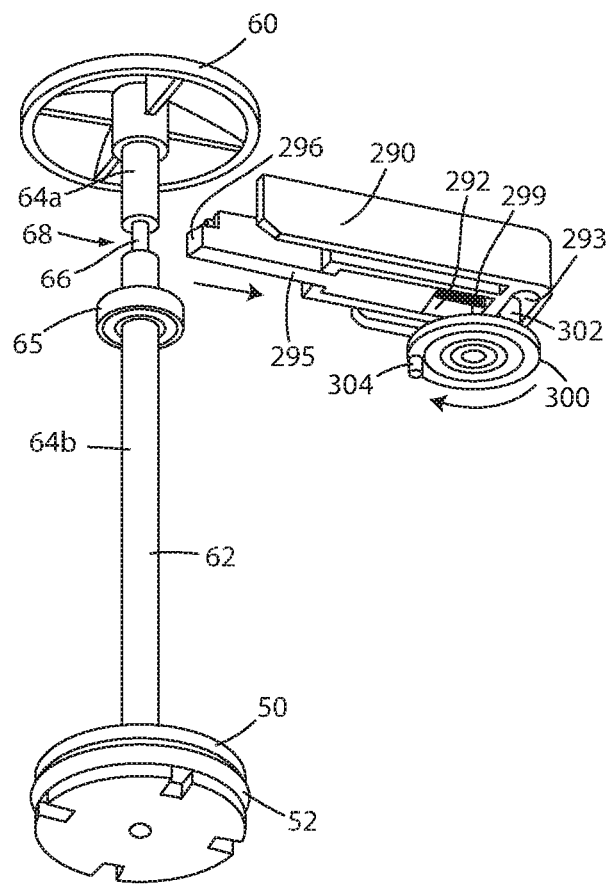
FIG. 21 is a perspective view of the relative position of the automatic lock/release mechanism when releasing the pump handle from being locked in the retracted position.
Figure 22:
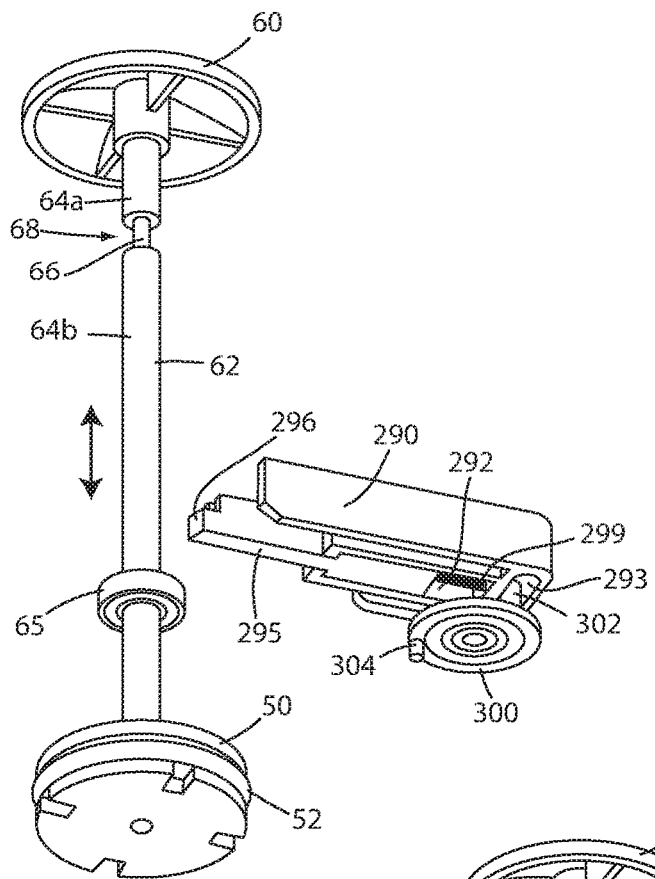
FIG. 22 is a perspective view of the relative position of the automatic lock/release mechanism when the pump handle has been released and is moved into the extended position.
Figure 23:
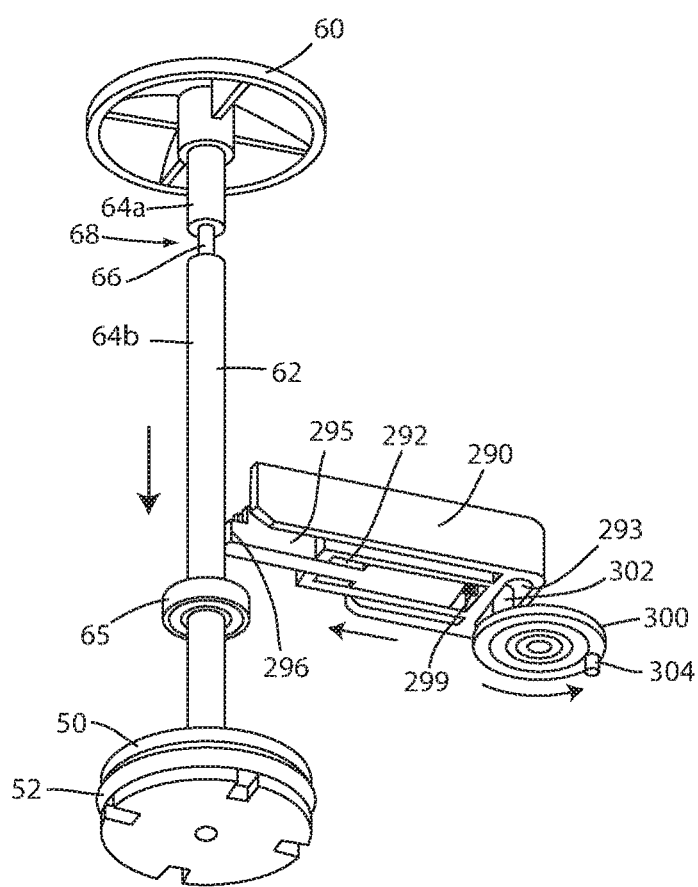
FIG. 23 is a perspective view of the relative position of the automatic lock/release mechanism when the pump handle is moved into the retracted position with the lock to be engaged.

To unlock the pump handle 60, controller 150 (FIG. 32) activates motor 250 whereby it causes drive wheel 300 to rotate. Rotation of drive wheel 300 translates into a linear motion of actuator 290 back away from pump shaft 62 as illustrated in FIG. 21. At this point, as shown in FIG. 22, pump handle 60 may be moved into an extended position by force of spring 70 and may be moved back into the retracted position by pressure applied by the user. The pump handle 60 may therefore be moved up and down to thereby generate a desired vacuum pressure level. In response to obtaining the target pressure level, controller 150 may activate motor 250 to rotate drive wheel 300 to thereby move actuator 290 toward pump shaft 62, as shown in FIG. 23. In the position shown in FIG. 23, pump handle 60 is shown in the extended position. In this case, spring 290 biases latch 295 toward shaft 62 such that catch 296 rides along the outer surface of the lower portion 64b of shaft 62. As pump handle 62 is pressed downward, catch 296 rides along the surface of lower portion 64b until such a point that it engages notch 68 whereby spring 299 pushes catch 296 into notch 68 to then lock the pump handle 60 in the retracted position as shown in FIG. 20.

Figure 30:
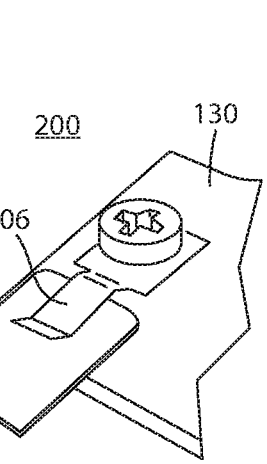
FIG. 30 is an enlarged perspective view of a portion of the circuit board shown in FIG. 29 with the activation mechanism in position to render the portable pump inactive.
Figure 31:
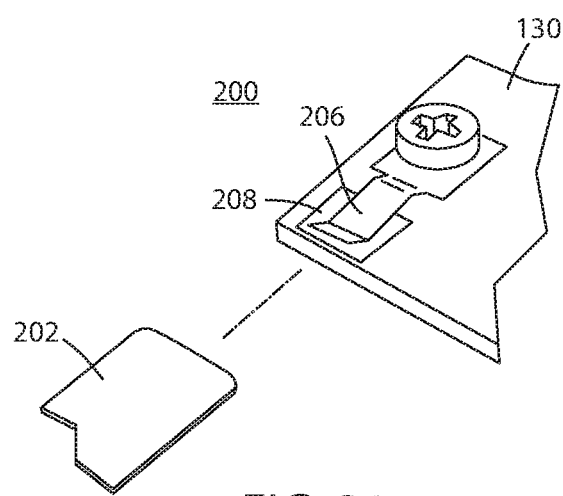
FIG. 31 is an enlarged perspective view of a portion of the circuit board shown in FIG. 29 with the activation mechanism in position to render the portable pump active.

As discussed above, portable pump 10 may further include an activation mechanism 200. Activation mechanism 200 is provided to conserve the use of the batteries 210 when the pump has not yet been activated. Further, by requiring user action to activate portable pump 10, controller 150 may activate an end-of-life timer that will cause the portable pump 10 to shut down after a predetermined amount of time (e.g., seven days) to signify the end of the intended life of portable pump 10. As shown in FIGS. 26-31, activation mechanism 200 may include a pull tab 202 that extends into a slot 204 formed in upper shell 16. As shown in FIG. 30, when pull tab 202 resides in slot 204, one end thereof extends between a spring contact 206 and a fixed contact 208 (FIG. 31) provided on circuit board 130. Pull tab 202 is preferably made of an electrically nonconductive material so as to interrupt the electrical connection between spring contact 206 and fixed contact 208. Contacts 206 and 208 may be provided between batteries 210 and a power supply 310 that in turn supplies power to the various electrical components of pump 10 as shown in FIG. 32. Thus, when a user wishes to activate portable pump 10, they may simply pull out pull tab 202 from slot 204, which causes spring contact 206 to connect to fixed contact 208 and thereby connect batteries 210 to power supply 310. Power supply 310 would then provide power to controller 150 and the various other components of the electrical circuit shown in FIG. 32, for example. This would wake up controller 150 which would then execute the method shown in FIG. 33.

Figure 33:
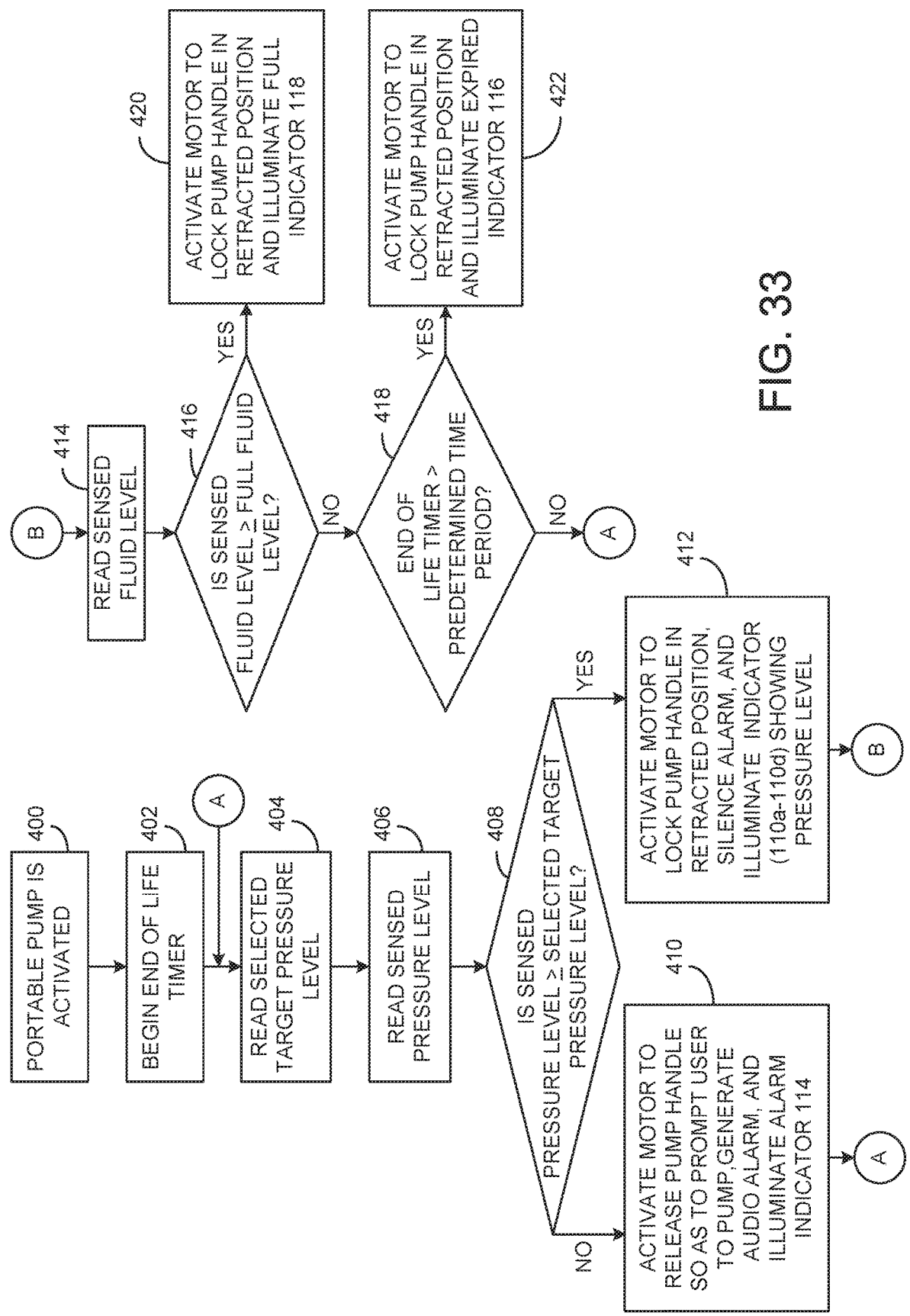
FIG. 33 is a flow diagram illustrating the methods/processes as performed by the controller shown in FIG. 32.

As shown in FIG. 33, controller 150 executes the depicted routine upon the portable pump 10 being activated in step 400. At this point, controller 150 begins an end-of-life timer in step 402. Next, controller 150 determines from pressure selection input mechanism 120 what is the selected target pressure level in step 404. Controller 150 then reads the sensed pressure level from pressure sensor 100 in step 406.

In step 408, controller 150 determines if the sensed pressure level has reached the selected target pressure level. If it has not reached the target pressure level (as would be the case right after the pump is initially activated), controller 150 proceeds to step 410 whereby it activates motor 250 to in turn cause automatic lock/release mechanism 80 to release pump handle 60, which is sprung into the extended position by spring 70 so as to prompt the user to begin manual pumping. In addition, controller 150 may cause audio alarm 170 to generate an alarm and may further activate alarm indicator light 114. Controller 150 then returns to step 404 in which it continues to determine whether the target pressure level that is selected has changed while then reading the sensed pressure level in step 406 and determining whether the sensed pressure level has yet reached the selected target pressure level. Thus, controller 150 continues to loop through steps 404-410 until such time that the user has pumped pump handle 60 enough times that the sensed pressure level has reached the selected target pressure level as determined in step 408.

Once the sensed pressure level has reached the selected target pressure level, controller 150 proceeds to step 412 whereby it activates motor 250 in order to cause automatic lock/release mechanism 80 to lock pump handle 60 in the retracted position. In addition, controller 150 may silence audio alarm 170 and may extinguish alarm indicator light 114 while illuminating one of pressure level indicator lights 110a-110d corresponding to either the selected target pressure level or the sensed pressure level.

After step 412, controller 150 proceeds to step 414 where it will read the sensed fluid level using fluid level sensor 160. In step 416, controller 150 will determine if the sensed fluid level has reached a full fluid level. As noted previously, this would occur in the event that the fluid level reaches the ends of pins 272a and 272b allowing current to flow through the fluid in canister 20 that may then be sensed by controller 150. If the fluid level has not yet reached the ends of pins 272a and 272b, controller 150 may proceed to step 418 whereby it determines whether the end-of-life timer has reached the predetermined time period representing the intended lifetime of portable pump 10. If the timer has not reached the predetermined time period, which may, for example, be seven days, controller 150 returns to step 404 where it will continue to loop through steps 404-418 so long as the pressure level as sensed by pressure sensor 100 does not fall below the selected target pressure level, the sensed fluid level does not exceed the full fluid level, or the end-of-life timer has not expired. If the pressure level falls below the selected target pressure level, controller determines this in step 408 and will proceed to step 410 whereby it will reactivate motor 250 to release the pump handle, generate an audio alarm 170, and illuminate alarm indicator light 114 to prompt the user to begin pumping.

In the event that the canister 20 becomes full of fluid such that the fluid level sensor 160 senses a full fluid level, controller 150 will then proceed to step 420 whereby it may activate motor 250 to lock the pump handle in the retracted position if it is not already locked in the retracted position and will illuminate full indicator light 118. Alternatively, controller 150 may control automatic lock/release mechanism 80 by activating motor 250 to release the pump handle such that the pump handle is moved into the extended position when the sensed fluid level reaches the predetermined level. This latter option provides the advantage of further prompting the user to attend to the device. At this point, because portable pump 10 is designed to be disposable, the user would no longer be able to utilize the pump and it would effectively shut down. Controller 150 may generate an audio alarm to further draw the user's attention to the full indicator light 118 so that they may dispose of portable pump 10 appropriately.

In the event that controller 150 determines in step 418 that the end-of-life timer has exceeded the predetermined time period, it proceeds to step 422 whereby it may activate motor 250 to lock pump handle 60 in the retracted position if it is not already so locked while illuminating expired indicator light 116. It may further activate audio alarm 170. As with step 420, in step 422, controller 150 effectively shuts down portable pump 10 while prompting the user to dispose of the pump appropriately. Alternatively, controller 150 may automatically shut down the portable pump by controlling automatic lock/release mechanism 80 by activating motor 250 to release the pump handle such that the pump handle moves into the extended position. This latter option provides the advantage of further prompting the user to dispose of the device.

Controller 150 may further be configured to monitor status button 115 to determine if it has been held down for a predetermined time period (e.g., 2 seconds). If controller 150 determines that status button 115 has been pushed down for this predetermined time period, it may enter a silent mode and silence any audio alarm 170. When in the silent mode, the audio alarm 170 will no longer sound from the device until pressure is reapplied the pump. This is useful for situations where the wound dressing has fallen off of the patient's wound site and they cannot fix the problem. Instead of listening to the alarm sound continuously until they can see the doctor, they can hold down the status button 115 for 2 seconds to enter silent mode. When in the silent mode, the alarm indicator light 114 will continue to flash on the device, but the alarm will no longer sound. The pump handle will stay in the extended position because pressure cannot be reapplied. Once the issue is resolved and pressure is reapplied and the handle is locked in the retracted position, controller 150 will automatically exit the silent mode and continue to function normally, meaning the next time pressure is lost the pump will audibly alarm. Thus, the silent mode is only active until the next time pressure is applied.

Figure 34:
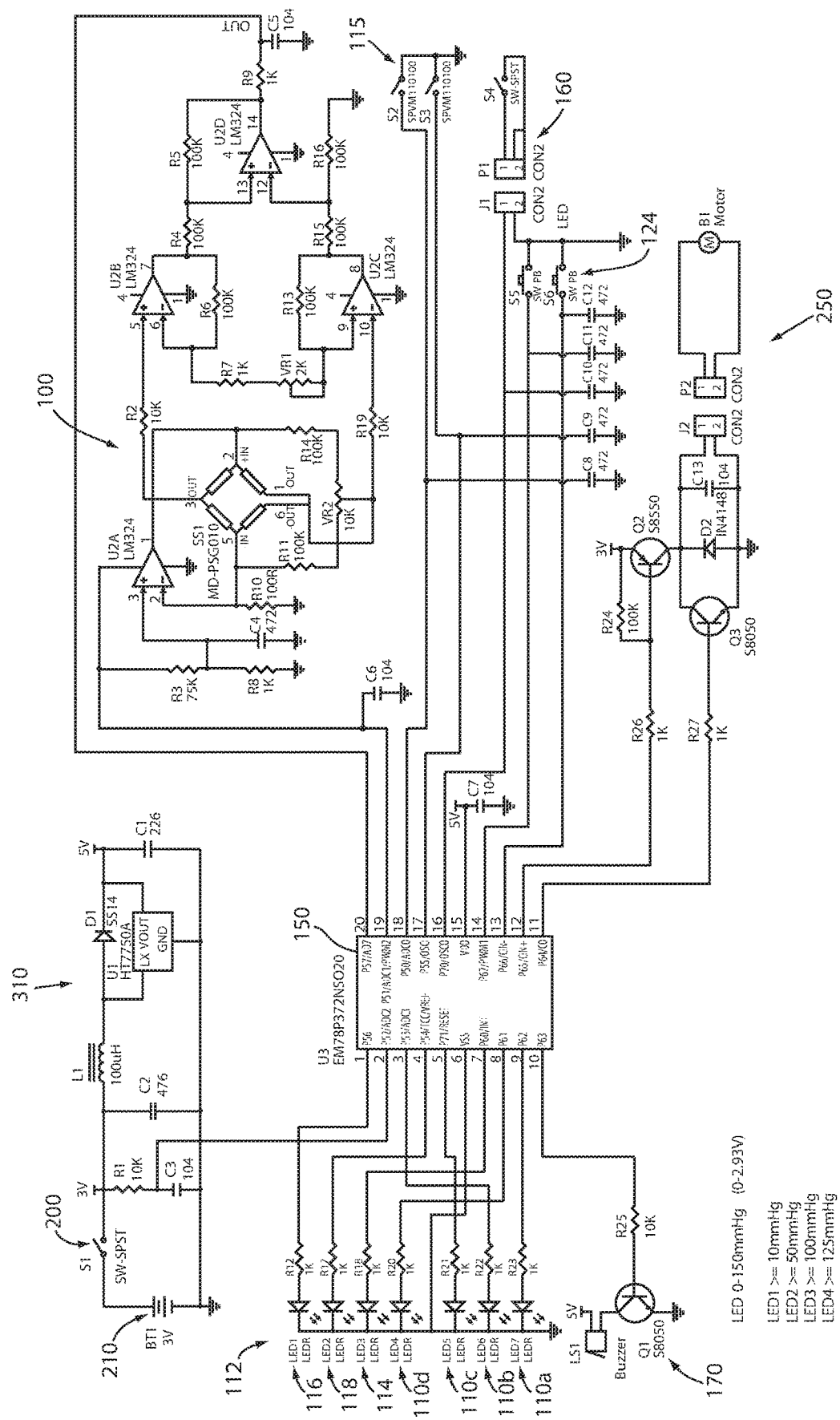
FIG. 34 is an electric circuit diagram in schematic form of the electrical circuit components corresponding to those shown in FIG. 32 in bock form.

FIG. 34 represents an example of an electrical circuit that may be used to implement the electrical circuit shown in FIG. 32. It will be appreciated, however, that the circuitry shown in FIG. 32 may be implemented using various alternative constructions.

The portable pump and all its components may be treated with an antimicrobial treatment solution. In a preferred form, the antimicrobial treatment solution contains 30-50 percent by volume isopropyl alcohol and 50-70 percent by volume antimicrobial treatment substance, which is preferably a silane quaternary ammonium salt having an unreacted organofunctional silane. If the antimicrobial treatment solution is applied by spraying or dipping, the solution most preferably includes 50 percent by volume isopropyl alcohol and 50 percent by volume of the unreacted antimicrobial treatment substance. If the solution is applied using the wipes, the solution is preferably 30 percent by volume isopropyl alcohol and 70 percent by volume of the unreacted antimicrobial treatment substance.

The isopropyl alcohol may have a concentration of 70-90 percent by volume. By providing the unreacted organofunctional silane in isopropyl alcohol, the organofunctional silane does not react with the wipe substrates or the inside of the wipe container such that it is free to later react and permanently covalently bond with the inner and outer surfaces 50 of the vascular access products. Isopropyl alcohol is preferred as it evaporates quickly once the solution is wiped onto the treated surface to allow the unreacted organofunctional silane to more quickly react with the treated surface.

The preferred organofunctional silane quaternary ammonium salt also prevents odor, staining and product deterioration that may be associated with microbe contamination. The preferred organofunctional silane quaternary ammonium salt is also beneficial because it permanently bonds to a treated surface, covers a broad spectrum of activity with no negative effects or drawbacks, and is easily incorporated and easily verifiable.

The preferred organofunctional silane quaternary ammonium salt is designed to react and create a covalent bond with the surfaces of the plastic components. The reacted substance is held onto those surfaces until the covalent bond is broken. Tests have shown that most industrial cleaners or disinfectants will not remove the preferred antimicrobial treatment substance. The method of removal is by abrasion.

The preferred silane quaternary ammonium salt includes an active ingredient of 3-(trimethoxysilyl) propyldimethyloctadecyl ammonium chloride and other inert ingredients. The silane quaternary ammonium salt preferably includes about 0.1 to 50 percent by weight of the 3-(trimethoxysilyl) propyldimethyloctadecyl ammonium chloride and most preferably includes about 5 percent by weight of the 3-(trimethoxysilyl) propyldimethyloctadecyl ammonium chloride. Such silane quaternary ammonium salts are available from Aegis Environments of Midland, Mich., which is identified as "AEM 5772-5 Antimicrobial," and from Piedmont Chemical Industries I, LLC of High Point, N.C., which is identified as "PROMOFRESH X 105." The antimicrobial treatment solution with the isopropyl alcohol is available from MicrobeCare, LLC of Allendale, Mich., under the trademark MICROBECARE™.

The above described silane quaternary ammonium salt is preferred because it is an organofunctional silane antimicrobial treatment substance that is substantially free from arsenic, silver, tin, heavy metals and polychlorinated phenols; copper; or a silver-ion emitter. In addition, it not only eliminates bacteria on contact, but it remains on the treated surfaces 50 and kills any bacteria subsequently contacting these surfaces. Such treatment preferably lasts at least one week, more preferably several months, and most preferably indefinitely.

It will be understood by one having ordinary skill in the art that construction of the described device and other components is not limited to any specific material. Other exemplary embodiments of the device disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within the described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise. For example, although the manually-activated pump mechanism is described has having a pump handle that moves from an extended to a retracted position, other forms of pump handles may be provided such as a turning crank handle (similar to those used for casement windows) or a pivoting handle. Further, the handle may be eliminated altogether and replaced with a rubber bladder that can be manually squeezed to create a vacuum. In some of these cases the piston would also not be used. Moreover, pumping beyond the amount required to create the desired pressure could be prevented by closing a valve that allow air back in the bladder or that allows movement of other forms of handles.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the claims as interpreted according to the principles of patent law, including the doctrine of equivalents.

What is claimed is:

1. A portable pump for negative pressure wound therapy for drawing a vacuum from a wound site via a tube, the portable pump comprising:
    an inlet configured to attach the tube from the wound site;
    a canister in fluid communication with said inlet for collecting fluids drained from the wound site; and
    a manually-actuated pump mechanism for creating the vacuum, said manually-actuated pump mechanism comprising:
        a vacuum chamber in fluid communication with said canister;
        a piston disposed in said vacuum chamber;
        a pump handle coupled to said piston so as to move said piston in said vacuum chamber between a first position and a second position so as to create the vacuum, the pump handle moving between a retracted position and an extended position, wherein said piston is in the first position when said pump handle is in the retracted position and is in the second position when said pump handle is in the extended position; and
        a spring disposed in said vacuum chamber for biasing said piston into the second position such that the spring compresses as said piston is moved from the second position to the first position, wherein upon manually pumping said pump handle, said piston creates a vacuum so as to create the vacuum at the wound site and to draw any fluids from the wound site into said canister; and an automatic lock/release mechanism for selectively locking said pump handle in the retracted position and releasing said pump handle such that said spring pushes said piston into the second position and hence said pump handle into the extended position.

2. The portable pump of claim 1 and further comprising:
a pressure sensor for sensing a pressure level in said canister; and
a controller coupled to said pressure sensor and said automatic lock/release mechanism for locking said pump handle in the retracted position when the portable pump is inactive and when the sensed pressure level is at a target pressure level, and for releasing said pump handle when the sensed pressure level is below the target pressure level.

3. The portable pump of claim 1, wherein said pump handle includes a shaft having a narrowed section having a smaller diameter than adjacent sections, and wherein said automatic lock/release mechanism comprises:
a motor coupled to said controller;
an actuator for moving toward or away from said shaft of said pump handle when said motor is activated by said controller; and
a latch disposed at one end of said actuator for selective engagement/disengagement of said shaft, wherein said latch is biased against said shaft when said actuator is moved toward said shaft such that said shaft may slide along said latch until said narrowed section slides against said latch at which point said latch prevents said shaft from further movement and locks said pump handle into the locked position.

4. The portable pump of claim 3, wherein said automatic lock/release mechanism further comprises at least one gear turned when said motor is activated by said controller for translating rotation of said motor into movement of said actuator.

5. The portable pump of claim 4, wherein said motor is reversible whereby motor rotation in one direction moves said actuator toward said shaft and rotation of said motor in an opposite direction moves said actuator away from said shaft.

6. The portable pump of claim 1 and further comprising:
a pressure sensor for sensing a pressure level in said canister; and
a pressure level indicator for indicating the sensed pressure level in said canister.

7. The portable pump of claim 6 and further comprising:
an audio alarm; and
a controller coupled to said pressure sensor and said audio alarm for causing said audio alarm to generate an alarm when the sensed pressure level is below a target pressure level.

8. The portable pump of claim 7 and further comprising:
a fluid level sensor in said canister for sensing a level of fluid in said canister,
wherein said controller is coupled to said fluid level sensor for causing said audio alarm to generate an alarm when the sensed fluid level reaches a predetermined level.

9. The portable pump of claim 1 and further comprising:
a fluid level sensor in said canister for sensing a level of fluid in said canister;
an audio alarm; and
a controller coupled to said fluid level sensor and said audio alarm for causing said audio alarm to generate an alarm when the sensed fluid level reaches a predetermined level.

10. The portable pump of claim 1 and further comprising:
a fluid level sensor in said canister for sensing a level of fluid in said canister;
an audio alarm; and
a controller coupled to said fluid level sensor and said audio alarm for causing said audio alarm to generate an alarm when the sensed fluid level reaches a predetermined level, wherein said controller is further coupled to said automatic lock/release mechanism for controlling said automatic lock/release mechanism to lock said pump handle in the retracted position when the sensed fluid level reaches the predetermined level.

11. The portable pump of claim 1 and further comprising:
an activation mechanism for a user to activate the portable pump; and
a controller coupled to said automatic lock/release mechanism, said controller senses manipulation of said activation mechanism and responds to manipulation of said activation mechanism by controlling said automatic lock/release mechanism to release said pump handle from the retracted position.

12. The portable pump of claim 11, wherein said controller further responds to manipulation of said activation mechanism by tracking time during which the portable pump is activated and automatically shutting down the portable pump by controlling said automatic lock/release mechanism to lock said pump handle in the retracted position.

13. The portable pump of claim 1 and further comprising a check valve disposed between said vacuum chamber and said canister for preventing air from flowing from said vacuum chamber into said canister when said piston is moved from the first position to the second position and for allowing air to be drawn from said canister to said vacuum chamber when said piston is moved from the second position to the first position.

14. The portable pump of claim 13 and further comprising a pressure relief valve in communication with said vacuum chamber for venting air to atmosphere when said piston is moved from the first position to the second position whereby said piston may be repeatedly moved between the second position to the first position to generate the vacuum without pumping air back into said canister.

15. A portable pump for negative pressure wound therapy for drawing a vacuum from a wound site via a tube, the portable pump comprising:
an inlet configured to attach the tube from the wound site;
a canister in fluid communication with said inlet for collecting fluids drained from the wound site;
a manually-actuated pump mechanism for creating the vacuum, said manually-actuated pump mechanism comprising:
a vacuum chamber in fluid communication with said canister;
a piston disposed in said vacuum chamber; and
a pump handle coupled to said piston so as to move said piston in said vacuum chamber between a first position and a second position so as to create the vacuum, the pump handle moving between a retracted position and an extended position, wherein said piston is in the first position when said pump handle is in the retracted position and is in the second position when said pump handle is in the extended position, wherein upon manually pumping said pump handle, said piston creates a vacuum so as to create the vacuum at the wound site and to draw any fluids from the wound site into said canister; and an automatic lock/release mechanism for selectively locking said pump handle in the retracted position and releasing said pump handle such said piston may be moved into the second position and hence said pump handle is moved into the extended position.

16. The portable pump of claim 15 and further comprising:
an activation mechanism for a user to activate the portable pump; and
a controller is coupled to said automatic lock/release mechanism, said controller senses manipulation of said activation mechanism and responds to manipulation of said activation mechanism by controlling said automatic lock/release mechanism to release said pump handle from the retracted position.

17. The portable pump of claim 16, wherein said controller further responds to manipulation of said activation mechanism by tracking time during which the portable pump is activated and automatically shutting down the portable pump by controlling said automatic lock/release mechanism to lock said pump handle in the retracted position.

18. The portable pump of claim 15 and further comprising:
a fluid level sensor in said canister for sensing a level of fluid in said canister;
an audio alarm; and
a controller coupled to said fluid level sensor and said audio alarm for causing said audio alarm to generate an alarm when the sensed fluid level reaches a predetermined level, wherein said controller is further coupled to said automatic lock/release mechanism for controlling said automatic lock/release mechanism to lock said pump handle in the retracted position when the sensed fluid level reaches the predetermined level.

19. The portable pump of claim 15 and further comprising:
a pressure sensor for sensing a pressure level in said canister; and
a controller coupled to said pressure sensor and said automatic lock/release mechanism for locking said pump handle in the retracted position when the portable pump is inactive and when the sensed pressure level is at a target pressure level, and for releasing said pump handle when the sensed pressure level is below the target pressure level.

20. The portable pump of claim 15, wherein said pump handle includes a shaft having a narrowed section having a smaller diameter than adjacent sections, and wherein said automatic lock/release mechanism comprises:
a motor coupled to said controller;
an actuator for moving toward or away from said shaft of said pump handle when said motor is activated by said controller; and
a latch disposed at one end of said actuator for selective engagement/disengagement of said shaft, wherein said latch is biased against said shaft when said actuator is moved toward said shaft such that said shaft may slide along said latch until said narrowed section slides against said latch at which point said latch prevents said shaft from further movement and locks said pump handle into the locked position.

21. The portable pump of claim 20, wherein said automatic lock/release mechanism further comprises at least one gear turned when said motor is activated by said controller for translating rotation of said motor into movement of said actuator.

22. The portable pump of claim 21, wherein said motor is reversible whereby motor rotation in one direction moves said actuator toward said shaft and rotation of said motor in an opposite direction moves said actuator away from said shaft.

23. A portable pump for negative pressure wound therapy for drawing a vacuum from a wound site via a tube, the portable pump comprising:
an inlet configured to attach the tube from the wound site;
a canister in fluid communication with said inlet for collecting fluids drained from the wound site;
a pressure sensor for sensing a pressure level in said canister;
a pressure level indicator for indicating the sensed pressure level in said canister;
a manually-actuated pump mechanism for creating the vacuum, wherein said manually-actuated pump mechanism comprises:
a vacuum chamber in fluid communication with said canister:
a piston disposed in said vacuum chamber; and
a pump handle coupled to said piston so as to move said piston in said vacuum chamber between a first position and a second position so as to create the vacuum, the pump handle moving between a retracted position and an extended position, wherein said piston is in the first position when said pump handle is in the retracted position and is in the second position when said pump handle is in the extended position, wherein upon manually pumping said pump handle, said piston creates a vacuum so as to create the vacuum at the wound site and to draw any fluids from the wound site into said canister; and
an automatic lock/release mechanism for selectively locking said pump handle in the retracted position and releasing said pump handle such that said piston may be moved into the second position and hence said pump handle is moved into the extended position.

24. The portable pump of claim 23 and further comprising:
a controller coupled to said pressure sensor and said automatic lock/release mechanism for locking said pump handle in the retracted position when the portable pump is inactive and when the sensed pressure level is at a target pressure level, and for releasing said pump handle when the sensed pressure level is below the target pressure level.

25. The portable pump of claim 23 and further comprising:
an audio alarm; and
a controller coupled to said pressure sensor and said audio alarm for causing said audio alarm to generate an alarm when the sensed pressure level is below a target pressure level.

26. The portable pump of claim 25 and further comprising a push button, wherein said controller is further configured to silence said audio alarm in response to activation of said push button.

27. The portable pump of claim 23 and further comprising:
a gelling agent provided in said canister for absorbing the collected fluids.

28. A portable pump for negative pressure wound therapy for drawing a vacuum from a wound site via a tube, the portable pump comprising:
an inlet configured to attach the tube from the wound site;

a canister in fluid communication with said inlet for collecting fluids drained from the wound site;
a pressure sensor for sensing a pressure level in said canister;
a manually-actuated pump mechanism for creating the vacuum, wherein said manually-actuated pump mechanism comprises:
   a vacuum chamber in fluid communication with said canister;
   a piston disposed in said vacuum chamber; and
   a pump handle coupled to said piston so as to move said piston in said vacuum chamber between a first position and a second position so as to create the vacuum, the pump handle moving between a retracted position and an extended position, wherein said piston is in the first position when said pump handle is in the retracted position and is in the second position when said pump handle is in the extended position, wherein upon manually pumping said pump handle, said piston crates a vacuum so as to create the vacuum at the wound site and to draw any fluid from the wound site into said canister;
a pressure selection input mechanism for allowing a target pressure level to be selected from one of a plurality of different target pressure levels;
a controller coupled to said pressure sensor and said pressure selection input mechanism for prompting the user to manually actuate said pump mechanism when the sensed pressure level is below the selected target pressure level; and
an automatic lock/release mechanism for selectively locking said pump handle in the retracted position and releasing said pump handle such that said piston may be moved into the second position and hence said pump handle is moved into the extended position.

29. The portable pump of claim 28 and further comprising:
an audio alarm,
wherein said controller is coupled to said audio alarm for causing said audio alarm to prompt the user to manually actuate said pump mechanism by generating an alarm when the sensed pressure level is below the selected target pressure level.

30. The portable pump of claim 28, wherein said controller is coupled to said automatic lock/release mechanism for prompting the user to manually pump said pump handle by releasing said pump handle when the sensed pressure level is below the selected target pressure level.

31. The portable pump of claim 28, wherein said controller is coupled to said automatic lock/release mechanism for locking said pump handle in the retracted position when the sensed pressure level is at the selected target pressure level.

32. A portable pump for negative pressure wound therapy for drawing a vacuum from a wound site via a tube, the portable pump comprising:
an inlet configured to attach the tube from the wound site;
a canister in fluid communication with said inlet for collecting fluids drained from the wound site;
a fluid level sensor in said canister for sensing a level of fluid in said canister;
an audio alarm;
a controller coupled to said fluid level sensor and said audio alarm for causing said audio alarm to generate an alarm when the sensed fluid level reaches a predetermined level; and
a manually-actuated pump mechanism for creating the vacuum, wherein said manually-actuated pump mechanism comprises:
   a vacuum chamber in fluid communication with said canister:
   a piston disposed in said vacuum chamber; and
   a pump handle coupled to said piston so as to move said piston in said vacuum chamber between a first position and a second position so as to create the vacuum the pump handle moving between a retracted position and an extended position, wherein said piston is in the first position when said pump handle is in the retracted position and is in the second position when said pump handle is in the extended position, wherein upon manually pumping said pump handle, said piston creates a vacuum so as to create the vacuum at the wound site and to draw any fluids from the wound site into said canister; and
an automatic lock/release mechanism for selectively locking said pump handle in the retracted position and releasing said pump handle such that a spring pushes said piston into the second position and hence said pump handle into the extended position.

33. The portable pump of claim 32, wherein said controller is further coupled to said automatic lock/release mechanism for controlling said automatic lock/release mechanism to lock said pump handle in the retracted position when the sensed fluid level reaches the predetermined level.

34. The portable pump of claim 32, wherein said controller is further coupled to said automatic lock/release mechanism for controlling said automatic lock/release mechanism to release said pump handle such that said pump handle is moved into the extended position when the sensed fluid level reaches the predetermined level.

35. A portable pump for negative pressure wound therapy for drawing a vacuum from a wound site via a tube, the portable pump comprising:
an inlet configured to attach the tube from the wound site;
a canister in fluid communication with said inlet for collecting fluids drained from the wound site;
a manually-actuated pump mechanism for creating the vacuum, said manually-actuated pump mechanism comprising:
   a vacuum chamber in fluid communication with said canister;
   a piston disposed in said vacuum chamber; and
   a pump handle coupled to said piston so as to move said piston in said vacuum chamber between a first position and a second position so as to create the vacuum, the pump handle moving between a retracted position and an extended position, wherein said piston is in the first position when said pump handle is in the retracted position and is in the second position when said pump handle is in the extended position, wherein upon manually pumping said pump handle, said piston creates a vacuum so as to create the vacuum at the wound site and to draw any fluids from the wound site into said canister;
a check valve disposed between said vacuum chamber and said canister for preventing air from flowing from said vacuum chamber into said canister when said piston is moved from the first position to the second position and for allowing air to be drawn from said canister to said vacuum chamber when said piston is moved from the second position to the first position; and an automatic lock/release mechanism for selectively locking said pump handle in the retracted position and releasing said pump handle such that said piston may be moved into the second position and hence said pump handle is moved into the extended position.

36. The portable pump of claim 35 and further comprising a pressure relief valve in communication with said vacuum chamber for venting air to atmosphere when said piston is moved from the first position to the second position whereby said piston may be repeatedly moved between the second position to the first position to generate the vacuum without pumping air back into said canister.

37. A portable pump for negative pressure wound therapy for drawing a vacuum from a wound site via a tube, the portable pump comprising:
- an inlet configured to attach the tube from the wound site;
- an activation mechanism for a user to activate the portable pump;
- a canister in fluid communication with said inlet for collecting fluids drained from the wound site;
- a manually-actuated pump mechanism for creating the vacuum, wherein said manually-actuated pump mechanism comprises:
  - a vacuum chamber in fluid communication with said canister:
  - a piston disposed in said vacuum chamber; and
  - a pump handle coupled to said piston so as to move said piston in said vacuum chamber between a first position and a second position so as to create the vacuum, the pump handle moving between a retracted position and an extended position, wherein said piston is in the first position when said pump handle is in the retracted position and is in the second position when said pump handle is in the extended position, wherein upon manually pumping said pump handle said piston creates a vacuum so as to create the vacuum at the wound site and to draw any fluids from the wound site into said canister;
- a controller configured to sense manipulation of said activation mechanism and to respond to manipulation of said activation mechanism by tracking time during which the portable pump is activated and automatically shutting down the portable pump upon expiration of a predetermined time period after manipulation of said activation mechanism; and
- an automatic lock/release mechanism for selectively locking said pump handle in the retracted position and releasing said pump handle such that said piston may be moved into the second position and hence said pump handle is moved into the extended position.

38. The portable pump of claim 37, wherein said controller is coupled to said automatic lock/release mechanism, said controller automatically shuts down the portable pump by controlling said automatic lock/release mechanism to lock said pump handle in the retracted position.

39. The portable pump of claim 37, wherein said controller is coupled to said automatic lock/release mechanism, said controller automatically shuts down the portable pump by controlling said automatic lock/release mechanism to release said pump handle such that said pump handle moves into the extended position.

* * * * *

UNITED STATES PATENT AND TRADEMARK OFFICE
CERTIFICATE OF CORRECTION

PATENT NO. : 10,814,048 B2
APPLICATION NO. : 15/586385
DATED : October 27, 2020
INVENTOR(S) : Patrick E. Eddy et al.

Page 1 of 1

It is certified that error appears in the above-identified patent and that said Letters Patent is hereby corrected as shown below:

In the Claims

Column 20, Claim 23, Line 20, replace ":" with --;--.
Column 21, Claim 28, Line 22, replace "fluid" with --fluids--.
Column 22, Claim 32, Line 5, replace ":" with --;--.
Column 22, Claim 32, Line 9, after "vacuum" insert --,--.
Column 23, Claim 37, Line 25, replace ":" with --;--.
Column 24, Claim 37, Line 4, after "handle" insert --,--.

Signed and Sealed this
Eighth Day of November, 2022

Katherine Kelly Vidal
*Director of the United States Patent and Trademark Office*